(12) United States Patent (10) Patent No.: US 12,636,498 B2
Case et al. (45) Date of Patent: May 26, 2026

(54) MONOPOLAR RECORDING IN A FULLY IMPLANTABLE MEDICAL SENSING DEVICE FOR PROGRAMMING GUIDANCE

(71) Applicant: Medtronic, Inc., Minneapolis, MN (US)

(72) Inventors: Michelle A. Case, Blaine, MN (US); Scott R. Stanslaski, Shoreview, MN (US); Caleb C. Zarns, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 457 days.

(21) Appl. No.: 17/805,364

(22) Filed: Jun. 3, 2022

(65) Prior Publication Data

US 2022/0387802 A1 Dec. 8, 2022

Related U.S. Application Data

(60) Provisional application No. 63/196,433, filed on Jun. 3, 2021.

(51) Int. Cl.
*A61N 1/36* (2006.01)
*A61N 1/05* (2006.01)
(52) U.S. Cl.
CPC ....... *A61N 1/36139* (2013.01); *A61N 1/0529* (2013.01)
(58) Field of Classification Search
CPC .......................... A61N 1/36139; A61N 1/0529
USPC .......................................................... 607/62
See application file for complete search history.

(56) References Cited

U.S. PATENT DOCUMENTS

| | | | |
|---|---|---|---|
| 7,177,690 B2 | 2/2007 | Woods et al. | |
| 7,783,340 B2 * | 8/2010 | Sanghera | A61N 1/3918 |
| | | | 600/512 |
| 9,457,195 B2 * | 10/2016 | Slavin | A61N 1/375 |
| 9,814,885 B2 | 11/2017 | Molnar et al. | |

(Continued)

FOREIGN PATENT DOCUMENTS

| | | |
|---|---|---|
| WO | 2002018009 A1 | 3/2002 |
| WO | 2019027517 A2 | 2/2019 |
| WO | 2021067498 A1 | 4/2021 |

OTHER PUBLICATIONS

International Search Report and Written Opinion of International Application No. PCT/US2022/072762 dated Oct. 25, 2022, 17 pp.

(Continued)

*Primary Examiner* — Michael J Lau
(74) *Attorney, Agent, or Firm* — Shumaker & Sieffert, P.A.

(57) ABSTRACT

Devices, systems, and techniques for monopolar recording of sensed electrical signals are disclosed. An example device includes sensing circuitry configured to sense electrical signals from a first plurality of electrode combinations, each of the first plurality of electrode combinations comprising a same reference electrode of the plurality of electrodes and at least one different sense electrode of the plurality of electrodes, the plurality of electrodes being associated with one or more leads. The example device includes processing circuitry configured to record the sensed electrical signals from the first plurality of electrode combinations. The processing circuitry is also configured to provide representations of the recorded sensed electrical signals.

19 Claims, 17 Drawing Sheets

(56)     References Cited

U.S. PATENT DOCUMENTS

| | | | | |
|---|---|---|---|---|
| 2006/0167497 A1* | 7/2006 | Armstrong | A61N 1/36082 | |
| | | | 607/2 | |
| 2008/0004675 A1* | 1/2008 | King | A61N 1/37247 | |
| | | | 607/116 | |
| 2012/0053659 A1* | 3/2012 | Molnar | A61N 1/025 | |
| | | | 607/62 | |
| 2013/0261706 A1* | 10/2013 | Mirro | A61N 1/36178 | |
| | | | 607/74 | |
| 2014/0135869 A1* | 5/2014 | Carlson | A61N 1/36067 | |
| | | | 607/45 | |
| 2015/0313487 A1* | 11/2015 | Single | A61B 5/24 | |
| | | | 600/554 | |
| 2016/0082261 A1* | 3/2016 | Moffitt | A61N 1/36132 | |
| | | | 607/46 | |
| 2016/0206380 A1 | 7/2016 | Sparks et al. | | |
| 2016/0346534 A1* | 12/2016 | Isaacson | A61N 1/36185 | |
| 2017/0049345 A1* | 2/2017 | Single | A61B 5/24 | |
| 2017/0056663 A1* | 3/2017 | Kaemmerer | A61N 1/36075 | |
| 2017/0173326 A1* | 6/2017 | Bloch | A61B 5/4836 | |
| 2019/0015660 A1* | 1/2019 | Zhang | G16H 20/40 | |
| 2019/0126046 A1 | 5/2019 | Dinsmoor et al. | | |
| 2019/0150840 A1* | 5/2019 | Darrow | A61N 1/0529 | |
| 2019/0321106 A1* | 10/2019 | Bergman | G06N 3/09 | |
| 2020/0038657 A1* | 2/2020 | Chang | A61N 1/36096 | |
| 2020/0046958 A1* | 2/2020 | Imran | A61M 5/14 | |
| 2020/0061371 A1* | 2/2020 | Raines | A61N 1/36182 | |
| 2020/0086114 A1 | 3/2020 | Willand et al. | | |
| 2020/0155833 A1* | 5/2020 | Villarta | A61N 1/0551 | |
| 2020/0179675 A1* | 6/2020 | Cass | H01R 43/24 | |
| 2020/0338351 A1* | 10/2020 | Panken | A61N 1/0534 | |
| 2020/0367761 A1* | 11/2020 | Akbari | A61B 5/4875 | |
| 2020/0384271 A1* | 12/2020 | Bocek | A61N 1/372 | |
| 2021/0121696 A1* | 4/2021 | Parker | G16H 20/40 | |

OTHER PUBLICATIONS

Invitation to Pay Additional Fees and, Where Applicable, Protest Fee from International Application No. PCT/US2022/072762 dated Sep. 1, 2022, 4 pp.

Communication pursuant to Article 94(3) EPC from counterpart European Application No. 22738831.1 dated Apr. 1, 2025, 5 pp.

Communication pursuant to Article 94(3) EPC from counterpart European Application No. 22738831.1 dated Dec. 2, 2025, 5 pp.

* cited by examiner

14

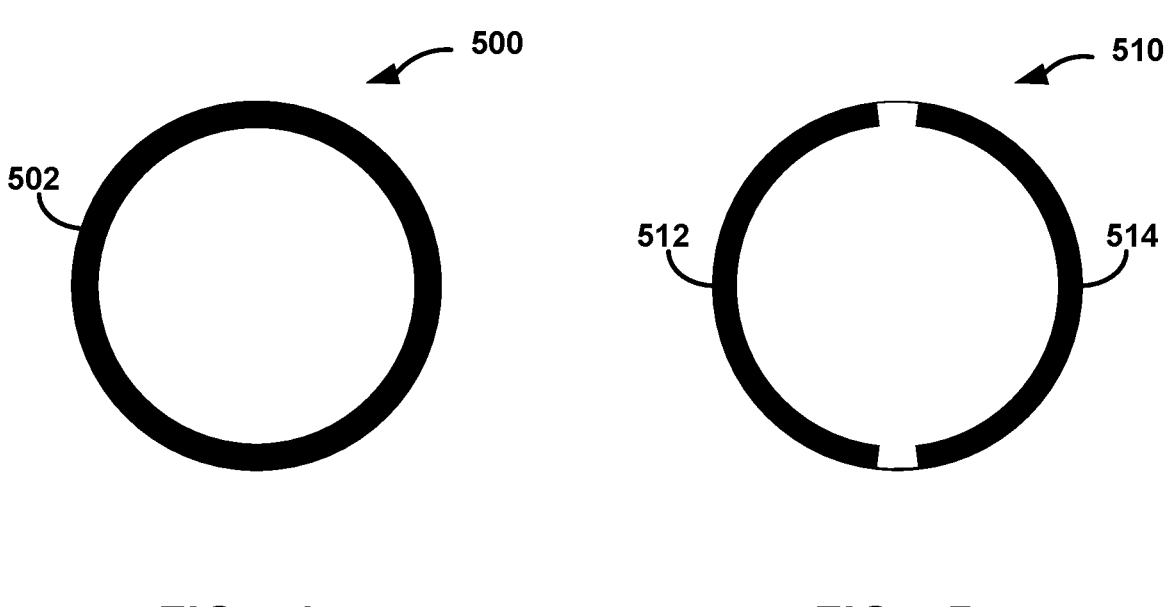
FIG. 5A                    FIG. 5B
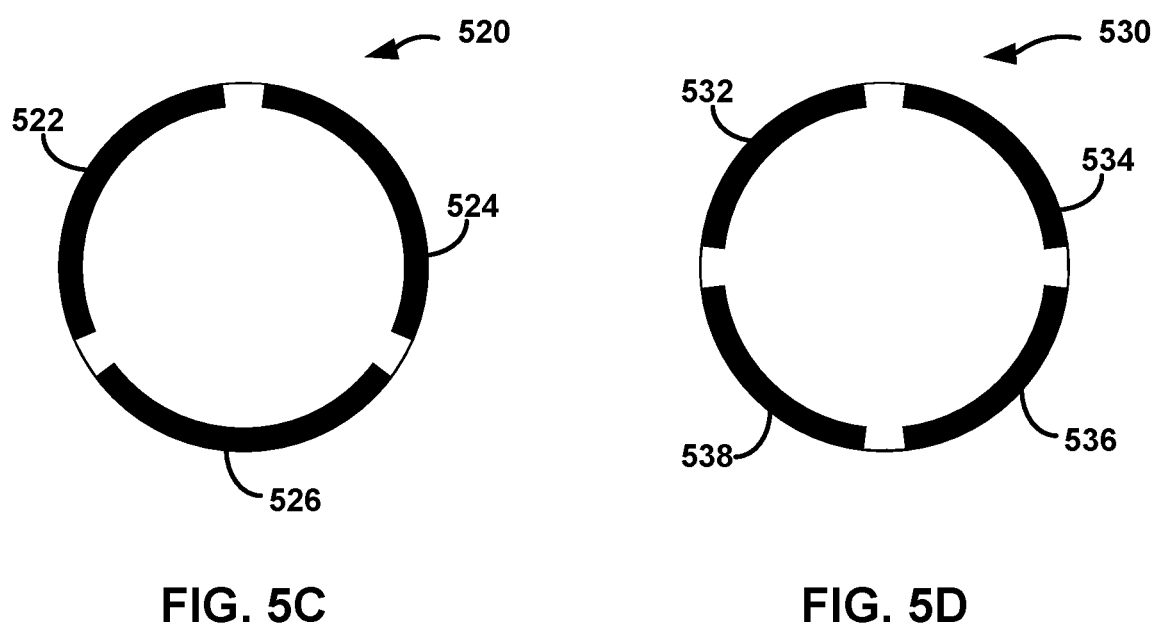
FIG. 5C                    FIG. 5D

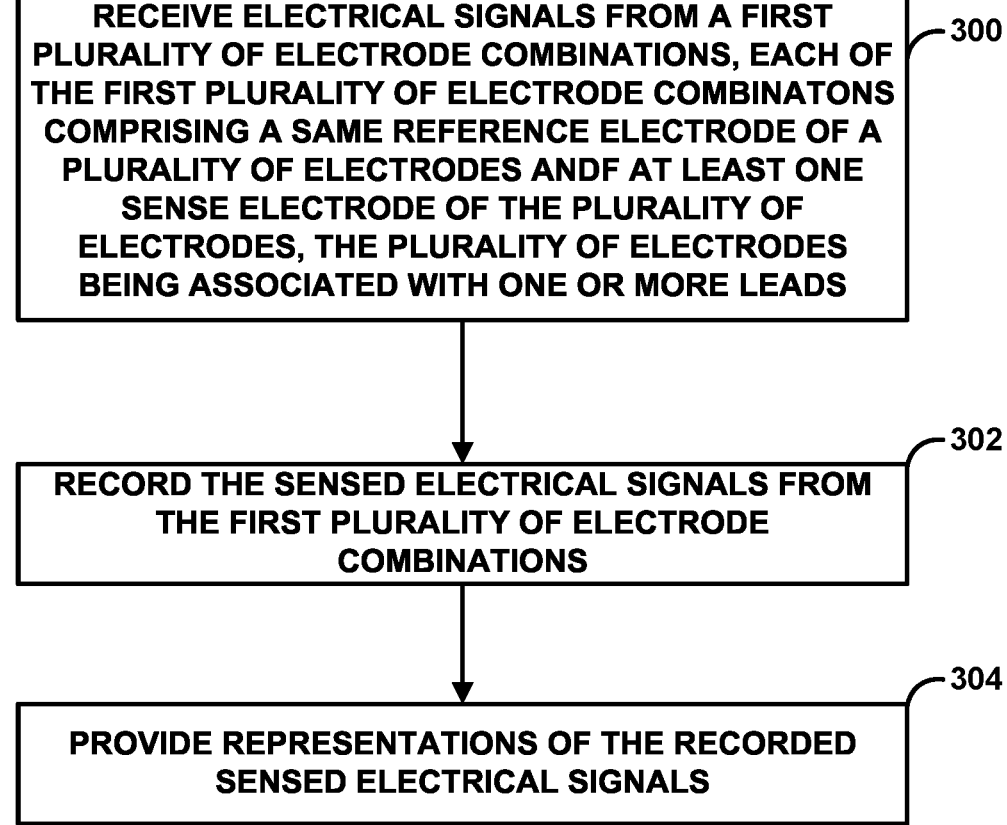

RECEIVE ELECTRICAL SIGNALS FROM A FIRST PLURALITY OF ELECTRODE COMBINATIONS, EACH OF THE FIRST PLURALITY OF ELECTRODE COMBINATONS COMPRISING A SAME REFERENCE ELECTRODE OF A PLURALITY OF ELECTRODES ANDF AT LEAST ONE SENSE ELECTRODE OF THE PLURALITY OF ELECTRODES, THE PLURALITY OF ELECTRODES BEING ASSOCIATED WITH ONE OR MORE LEADS ⌐300

RECORD THE SENSED ELECTRICAL SIGNALS FROM THE FIRST PLURALITY OF ELECTRODE COMBINATIONS ⌐302

PROVIDE REPRESENTATIONS OF THE RECORDED SENSED ELECTRICAL SIGNALS ⌐304

FIG. 13

PERFORM IMPEDANCE CHECK — 400

DETERMINE WHICH ELECTRODE IS A REFERENCE ELECTRODE — 402

DETERMINE WHETHER MAJOR ARTIFACTS ARE PRESENT — 404

DETERMINE AN LPS — 406

DETERMINE WHETHER A MINIMUM SEPARABILITY THRESHOLD BETWEEN A MAXIMUM SIGNAL AND MINIMUM SIGNAL IS MET — 408

DETECT PEAKS IN THE SIGNALS — 410

OUTPUT FOR DISPLAY AT LEAST A PORTION OF ONE OR MORE OF THE SIGNALS — 412

MONOPOLAR RECORDING IN A FULLY IMPLANTABLE MEDICAL SENSING DEVICE FOR PROGRAMMING GUIDANCE

This application claims priority to U.S. Provisional Application No. 63/196,433, filed Jun. 3, 2021, the entire contents of which is hereby incorporated by reference.

TECHNICAL FIELD

The disclosure relates to medical devices, and more specifically, sensing electrical signals from a patient.

BACKGROUND

Implantable medical devices, such as electrical stimulators or therapeutic agent delivery devices, have been proposed for use in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agents, insulin, pain relieving agents or anti-inflammatory agents to a target tissue site within a patient. In some therapy systems, an implantable electrical stimulator delivers electrical therapy to a target tissue site within a patient with the aid of two or more electrodes, that may be deployed by medical leads and/or on a housing of the electrical stimulator, or both. In some therapy systems, therapy may be delivered via particular combinations of the electrodes carried by leads and/or by the housing of the electrical stimulator.

During a programming session, that may occur during implantation of the medical device, during a trial session, or during an in-clinic or remote follow-up session after the medical device is implanted in the patient, a clinician may generate one or more therapy programs (also referred to as therapy parameter sets) that are found to provide efficacious therapy to the patient, where each therapy program may define values for a set of therapy parameters. A medical device may deliver therapy to a patient according to one or more stored therapy programs. In the case of electrical stimulation, the therapy parameters may define characteristics of the electrical stimulation waveform to be delivered. In examples in that electrical stimulation is delivered in the form of electrical pulses, for example, the therapy parameters may include an electrode configuration including an electrode combination and electrode polarities, an amplitude, that may be a current or voltage amplitude, a pulse width, and a pulse rate.

SUMMARY

In general, this disclosure is directed to devices, systems, and methods for utilizing brain signals, such as LFPs (local field potentials), to identify electrodes on one or more implantable leads that may be most appropriate for delivery of stimulation. For example, the system may sense signals between each electrode on a lead using a particular electrode as a reference (e.g., a reference electrode). Such sensing may be referred to as monopolar sensing. In some examples, the reference electrode is an electrode on a different lead than the lead including the sense electrode(s). In some examples, the reference electrode may be a distal most or proximal most electrode on the same lead as the sensing electrodes. In some examples, the system may perform the sensing of signals in this manner on each lead of the system. In this manner, the system may sense signals between different electrodes in order to highlight relevant differences between stimulation delivered via each of the electrodes. The system may then generate information regarding these signals and inform the clinician of these signals. The physician, or the system, may then determine parameters for stimulation including which electrodes to use as stimulation electrodes using these obtained signals (e.g., the LFP distribution) instead of having to test stimulation provided by each electrode combination. The use of LFP guided programming may reduce an amount of time required to program therapy. This may be particularly true when using segmented leads. Additionally, monopolar sensing may be less susceptible to electrocardiogram artifacts than bipolar sensing, resulting in less noisy sensed signals.

As one example, an implantable medical device includes sensing circuitry configured to sense electrical signals from a first plurality of electrode combinations, each of the first plurality of electrode combinations comprising a same reference electrode of a plurality of electrodes and at least one different sense electrode of the plurality of electrodes, the plurality of electrodes being associated with one or more leads; and processing circuitry configured to: record the sensed electrical signals from the first plurality of electrode combinations; and provide representations of the recorded sensed electrical signals.

As another example, a method includes receiving, by processing circuitry, electrical signals from a first plurality of electrode combinations, each of the first plurality of electrode combinations comprising a same reference electrode of a plurality of electrodes and at least one different sense electrode of the plurality of electrodes, the plurality of electrodes being associated with one or more leads; recording, by the processing circuitry, the sensed electrical signals from the first plurality of electrode combinations; and providing, by the processing circuitry, representations of the recorded sensed electrical signals.

As another example, a non-transitory computer-readable storage medium stores instructions that, when executed, cause processing circuitry to: receive electrical signals from a first plurality of electrode combinations, each of the first plurality of electrode combinations comprising a same reference electrode of a first plurality of electrodes of a first lead and at least one different sense electrode of a second plurality of electrodes of a second lead; record the sensed electrical signals from the first plurality of electrode combinations; and provide representations of the recorded sensed electrical signals.

The details of one or more examples are set forth in the accompanying drawings and the description below. Other features, objects, and advantages will be apparent from the description and drawings, and from the claims.

BRIEF DESCRIPTION OF DRAWINGS

FIGS. 5A, 5B, 5C, and 5D are conceptual cross-sectional diagrams of leads with example electrodes disposed around a perimeter of each lead at a particular axial positions.

FIG. 13 illustrates a flow diagram of an example method for selecting electrode combinations for stimulation by an implanting clinician, in accordance with one or more techniques of this disclosure.

DETAILED DESCRIPTION

Figure 1:
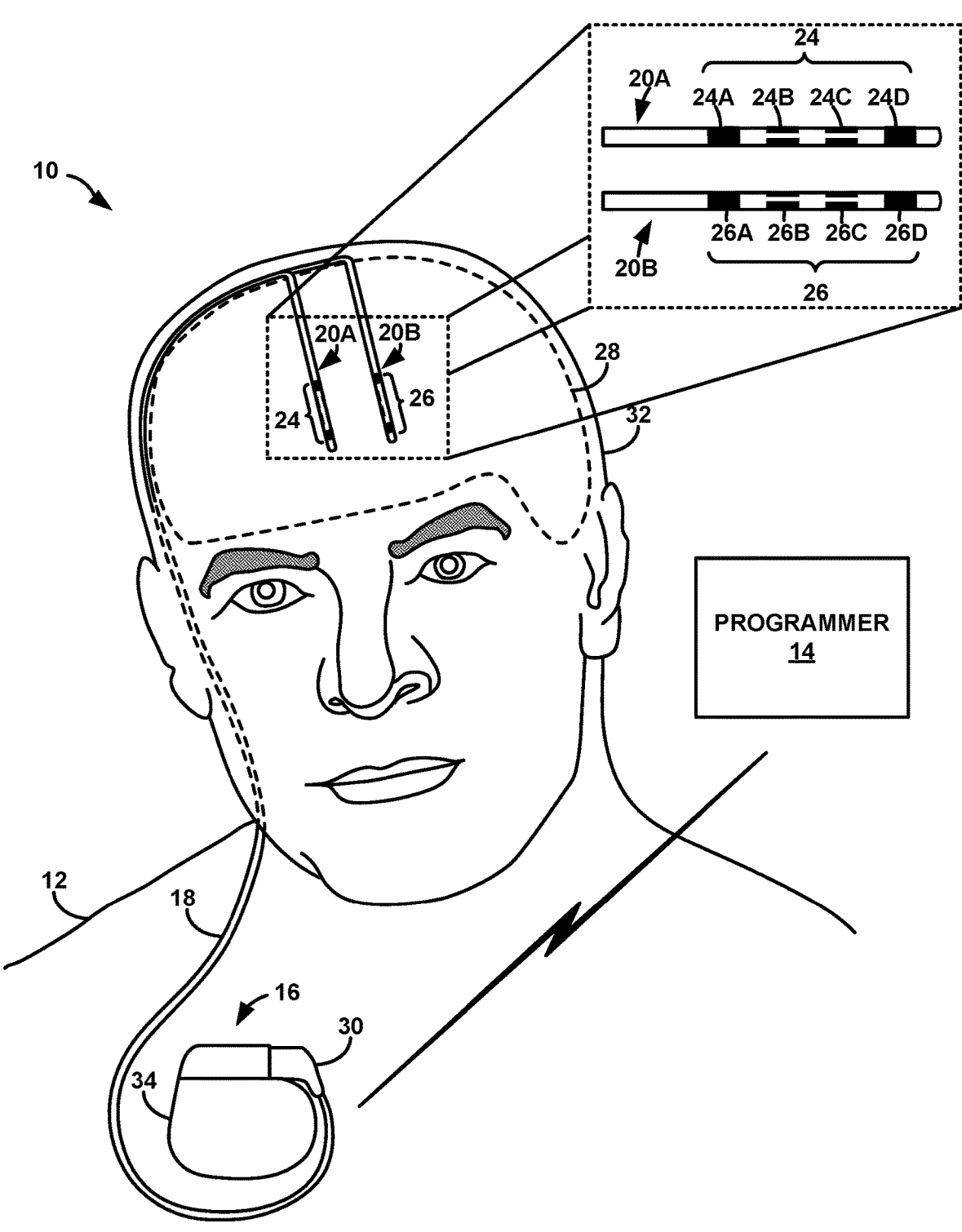
FIG. 1 is a conceptual diagram illustrating an example deep brain stimulation (DBS) system configured to deliver electrical stimulation therapy to a tissue site within a brain of a patient.

In general, the disclosure is directed to utilizing sensed electrical signals, such as LFPs within the brain, to identify which electrode or electrodes of a plurality of electrodes on an implantable lead may be appropriate to deliver electrical stimulation. While primarily described herein with respect to a brain, the techniques of this disclosure may be used to identify which electrode or electrodes on an implantable lead may be appropriate to deliver electrical stimulation to other parts of the anatomy, such as the spinal cord, pelvic floor, peripheral nerves, and the like.

Many brain disorders may be associated with abnormal brain function. In one example, Parkinson's Disease (PD) is a progressive neuro-degenerative disorder characterized by the depletion of dopaminergic neurons in the basal ganglia-thalamo-cortical network. As PD progresses, the manifestations of the disease may include one or more of the characteristic motor dysfunctions that include one or more of akinesia, bradykinesia, rigidity, and tremor. In some examples, deep brain stimulation (DBS) therapy may be used to deliver electrical stimulation to treat motor symptoms in medication-refractory PD patients. In some examples, DBS therapy may involve the unilateral or bilateral implantation of one or more leads into the brain to deliver electrical stimulation to target structures in the basal ganglia. Selection of effective stimulation parameters for DB S therapy may be time-consuming for both the clinician (e.g., a physician, nurse, or technician) and the patient. As such, it may be desirable to reduce the amount of time consumed to select stimulation parameters. In addition, the trial-and-error approach for determining appropriate electrode combinations and/or other stimulation parameters may subject the patient to undesirable side effects during this lengthy process and/or may result in less than optimal stimulation parameters, thus lessening the therapeutic value of any therapy delivered.

The target region associated with a disease (e.g., PD) may generate signals of interest (e.g., Beta waves that may be indicative of symptoms such as tremor in PD). As described herein, a system may sense signals between different combinations of electrodes in order to highlight relevant differences between the sensed signals from each of the electrodes. The system may then generate information regarding these signals, such as information that may be presented to a clinician and/or information used by the system to select parameter values for stimulation such as two or more stimulation electrodes. The sensed signals may be between electrodes at different circumferential positions and/or electrodes at different axial positions on one lead and a reference electrode on another lead (e.g., monopolar sensing). The clinician, or the system, may then determine parameters for stimulation based on one or more characteristics of these obtained signals instead of having to test stimulation provided by each electrode combination. For example, parameters for stimulation may include which electrodes are used for stimulation, polarity of the electrodes used for stimulation (e.g., anode or cathode), and parameters of the electrical stimulation signal, such as voltage or current amplitude, frequency, waveform shape, on/off cycling state (e.g., if cycling is "off," stimulation is always on, and if cycling is "on," stimulation is cycled on and off) and, in the case of electrical stimulation pulses, current or voltage pulse amplitude, pulse rate, pulse width, and other appropriate parameters such as duration or duty cycle.

For example, a Beta rhythm may be localized with the dorsal subthalamic nucleus (STN). It may be helpful to select stimulation electrodes that may generate an electric field that affects this oscillatory region of the brain, which may in some examples be stimulation electrodes that are positioned proximally or optimally relative to the region. The system may detect electrical signals between different electrode combinations and process the signals to generate spectral power characteristics for one or more frequencies. The system may then identify the electrode combinations, and thus axial (or level) and circumferential positions of the electrode combinations, associated with the spectral power characteristics indicative of stronger Beta waves. In some examples, the system may select the electrode combination associated with stronger Beta waves for targeted stimulation to this region of tissue. In addition, or alternatively, the system may present this information to a clinician to enable the clinician to review the LFPs sensed (and/or characteristics such as spectral power) from different electrode combinations. The clinician may then select an electrode combination associated with the stronger (e.g., larger amplitude spectral power) electrode amplitudes associated with Beta waves for subsequent sensing and/or stimulation therapy.

Each lead may have electrodes disposed at different axial positions along the length of the lead. These electrodes may be ring electrodes and/or segmented electrodes that only reside around a limited portion of the perimeter of the lead. In the case of segmented electrodes that only reside around a limited portion of the perimeter of the lead, at a given axial position, each lead may have electrodes at different circumferential positions (e.g., at different positions around the perimeter of the lead). Hence, two or more segmented electrodes may be positioned at the same axial position along the length of the lead (e.g., on the same level of the lead). As an illustration, a 1-3-3-1 lead would have, in order, a ring electrode at a first, most proximal axial level, three segmented electrodes at different circumferential positions of a second, more distal axial level, three segmented electrodes at different circumferential positions of a third, still more distal axial level, and a ring electrode at a fourth, most distal axial level. In some examples, the system may group electrodes together as one polarity, e.g., as a group of cathodes, for use with another electrode of another polarity, e.g., an anode, or vice versa. The system may perform such groupings in order to balance impedance between cathodes and anodes and improve sensing fidelity. In one example, to sense between an axial level of the lead with a ring electrode and another axial level with multiple smaller, segmented electrodes at different circumferential positions, the system may group together those electrodes at different circumferential positions to create a virtual ring electrode (also referred to herein as segmented electrodes in a ring mode) that may improve sensing between an actual ring electrode and the virtual ring electrode. The grouping together of those electrodes at different circumferential positions to create a virtual ring electrode may be referred to as a ring mode.

Sensing electrical signals between different electrodes, including electrodes at different axial positions and at different circumferential positions, may provide valuable information about where certain electrical signals (e.g., signals in the Beta frequency band or Beta waves, alpha waves, gamma waves, theta waves, and high frequency oscillations (HFO)) are originating from within tissue. In this manner, the system (or a clinician) may use this information to determine which electrodes (and/or other stimulation parameter values) should be used to deliver electrical stimulation therapy. In one example, the system may provide information representative of the sensed electrical signals via a display to enable a clinician to program stimulation more effectively and in less time than using trial-and-error approaches.

As part of generating the one or more therapy programs, a clinician may select which electrodes to use for stimulation. For example, a clinician may utilize the medical device to record sensed electrical signals between different pairs of electrodes on a single lead (e.g., bipolar sensing) and a display to display representations of the recorded bipolar sensed electrical signals. However, generating the one or more therapy programs based on the representations of the recorded bipolar sensed electrical signals may not be intuitive for many clinicians. Additionally, bipolar sensing may be susceptible to electrocardiogram artifacts which may result in noisy sensed electrical signals, further complicating the stimulation electrode selection process.

Alternatively, as part of generating the one or more therapy programs, a clinician may perform a review to test each electrode and the effect of stimulating using each electrode on the symptoms of a patient. However, this process may take as several hours and be uncomfortable for the patient. According to the techniques of this disclosure, a medical device may utilize monopolar sensing to assist a clinician in selecting appropriate electrodes to use for electrical stimulation therapy. The time it may take to complete the monopolar sensing may be as short as three minutes, thereby greatly reducing the time it may take to select the appropriate electrodes for stimulation, reducing the chance of error in selecting the appropriate electrodes, and/or reduce the uncomfortable effects for the patient. The techniques of this disclosure include using monopolar sensing to sense brain signals (or other signals) and process those signals so as to convert the brain signals into representations of the brain signals and to display the representations of the brain signals.

FIG. 1 is a conceptual diagram illustrating an example therapy system 10 that is configured to deliver therapy to patient 12 to manage a disorder of patient 12. Patient 12 ordinarily will be a human patient. In some cases, however, therapy system 10 may be applied to other mammalian or non-mammalian non-human patients. In the example shown in FIG. 1, therapy system 10 includes medical device programmer 14, implantable medical device (IMD) 16, lead extension 18, and one or more leads 20A and 20B (collectively "leads 20") with respective sets of electrodes 24, 26. IMD 16 includes a stimulation generator (not shown in FIG. 1) configured to generate and deliver electrical stimulation therapy to the STN region of brain 28 of patient 12 via electrodes 24 and/or 26 of leads 20A and 20B, respectively.

In the example shown in FIG. 1, therapy system 10 may be referred to as a deep brain stimulation (DBS) system because IMD 16 is configured to deliver electrical stimulation therapy directly to the STN within brain 28. DBS may be used to treat or manage various patient conditions, such as, but not limited to, seizure disorders (e.g., epilepsy), pain, migraine headaches, psychiatric disorders (e.g., major depressive disorder (MDD), bipolar disorder, anxiety disorders, post-traumatic stress disorder, dysthymic disorder, and obsessive compulsive disorder (OCD)), behavior disorders, mood disorders, memory disorders, mentation disorders, movement disorders (e.g., essential tremor or Parkinson's disease), Huntington's disease, Alzheimer's disease, or other neurological or psychiatric disorders and impairment of patient 12.

In the example shown in FIG. 1, IMD 16 may be implanted within a subcutaneous pocket in the pectoral region of patient 12. In other examples, 1 MB 16 may be implanted within other regions of patient 12, such as a subcutaneous pocket in the abdomen or buttocks of patient 12 or proximate the cranium of patient 12. Implanted lead extension 18 is coupled to circuitry in 1 MB 16 via proximal electrical contacts that connect to electrical terminals in connector block 30 (also referred to as a header). Lead extension 18 may include, for example, distal electrical contacts that electrically couple to proximal electrical contacts of leads 20A, 20B, which in turn may be coupled to respective electrodes 24, 26 via conductors within leads 20A, 20B. The proximal electrical contacts of leads 20A, 20B and the distal electrical contacts of lead extension 18 electrically couple the electrodes 24, 26 carried by leads 20 to the proximal contacts of lead extension 18 via conductors within the lead extension 18, and in turn to circuitry of IMD 16 via terminals in connector block 30. Lead extension 18 traverses from the implant site of IMB 16 within a chest cavity of patient 12, along the neck of patient 12 and through the cranium of patient 12 to access brain 28. IMD 16 may be constructed of a biocompatible material that resists corrosion and degradation from bodily fluids. IMD 16 may comprise a hermetically sealed housing 34 to substantially enclose components, such as a processor, a therapy module, and memory.

In the example shown in FIG. 1, leads 20 are implanted within the right and left hemispheres, respectively, of brain 28 in order to deliver electrical stimulation to one or more regions of brain 28, that may be selected based on many factors, such as the type of patient condition that therapy system 10 is implemented to manage. Other implant sites for leads 20 and IMB 16 are contemplated. For example, IMD 16 may be implanted on or within cranium 32 or leads 20 may be implanted within the same hemisphere at multiple target tissue sites or IMB 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 via any suitable technique, such as through respective burr holes in the skull of patient 12 or through a common burr hole in the cranium 32. Leads 20 may be placed at any location within brain 28 such that electrodes 24, 26 are capable of providing electrical stimulation to target therapy delivery sites within brain 28 during treatment. In the case of Parkinson's disease, for example, leads 20 may be implanted to deliver electrical stimulation to regions within the STN, either unilaterally or bilaterally. Target therapy delivery sites not located in brain 28 of patient 12 are also contemplated.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates therapy system 10 as including two leads 20A and 20B coupled to IMD 16 via lead extension 18, in some examples, therapy system 10 may include one lead or more than two leads.

In the examples shown in FIG. 1, electrodes 24A, 24D, 26A, and 26D of leads 20 are shown as ring electrodes. Ring electrodes may be relatively easy to program and may be capable of delivering an electrical field to any tissue adjacent to leads 20. Electrodes 24B, 24C, 26B, and 26C of leads 20 may have different configurations. For example, electrodes 24B, 24C, 26B, and 26C of leads 20 may each have a complex electrode array geometry that is capable of producing shaped electrical fields. An example of a complex electrode array geometry may include an array of segmented electrodes positioned at different axial positions along the length of a lead, as well as at different angular (i.e., circumferential) positions about the periphery, e.g., circumference, of the lead. The complex electrode array geometry may include multiple electrodes (e.g., partial ring or segmented electrodes), such as electrode 24B, 24C, 26B, and 26C that each include multiple individually programmable electrodes located at different positions around the perimeter of each respective lead 20. Although electrodes 24A, 24D, 26A, and 26D may be ring electrodes that each extend fully around the perimeter of the lead, any of these electrodes may be replaced, in other examples, by multiple electrodes located at different positions around the perimeter of the lead. Although electrodes 24B, 24C, 26B, and 26C may be include multiple electrodes (e.g., partial ring electrodes or segmented electrodes), any of these electrodes may be replaced by ring electrodes. By using electrodes disposed at different positions around the perimeter of the lead, IMD 16 may deliver directional stimulation, with electrical stimulation that may be directed in a specific direction from leads 20 to enhance therapy efficacy and reduce possible adverse side effects from stimulating a large volume of tissue. As a further example, the electrodes may be pad electrodes, that may be carried on a paddle lead or a cylindrical lead.

As illustrated in the example of FIG. 1, the set of electrodes 24 of lead 20A may include electrodes 24A, 24B, 24C, and 24D, and the set of electrodes 26 of lead 20B may include electrodes 26A, 26B, 26C, and 26D. In some examples, each of electrodes 24 and 26 may be configured to independently deliver electrical stimulation.

In some examples, outer housing 34 of IMD 16 may include one or more stimulation and/or sensing electrodes. Some or all of the electrodes may be used for both sensing and stimulation, or some electrodes may be dedicated to sensing while some other electrodes may be dedicated to stimulation. Housing 34 may comprise an electrically conductive material that is exposed to tissue of patient 12 when IMD 16 is implanted in patient 12, or an electrode may be attached to housing 34. Hence, in some examples, electrode combinations for stimulation and/or sensing may be formed by combinations of one or more electrodes on a lead or leads and one or more electrodes on housing 34 of IMD 16, or by combinations of two or more electrodes on a lead or leads. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs (also referred to herein as "set of stimulation parameter values"). A stimulation therapy program may define one or more electrical stimulation parameter values for therapy generated by a stimulation generator (not shown in FIG. 1) of IMD 16 and delivered from IMD 16 to a target therapy delivery site within patient 12 via one or more electrodes 24, 26. The electrical stimulation parameters may define an aspect of the electrical stimulation therapy, and may include, for example, voltage or current amplitude of an electrical stimulation signal, a charge level of an electrical stimulation, a frequency of the electrical stimulation signal, waveform shape, on/off cycling state (e.g., if cycling is "off," stimulation is always on, and if cycling is "on," stimulation is cycled on and off) and, in the case of electrical stimulation pulses, current or voltage pulse amplitude, pulse rate, pulse width, and other appropriate parameters such as duration or duty cycle. In addition, if different electrodes are available for delivery of stimulation, an electrode combination may further characterize a therapy parameter of a therapy program, that may define selected electrodes 24, 26 and their respective polarities. In some examples, stimulation may be delivered using a continuous waveform and the stimulation parameters may define this waveform, although stimulation will generally be described herein as being defined by stimulation pulses.

In addition to being configured to deliver therapy to manage a disorder of patient 12, therapy system 10 may be configured to sense bioelectrical brain signals or another physiological parameter of patient 12. For example, IMD 16 may include a sensing circuitry that is configured to sense bioelectrical brain signals within one or more regions of brain 28 via a subset of electrodes 24, 26, another set of electrodes, or both. Accordingly, in some examples, electrodes 24, 26 may be used to deliver electrical stimulation from the stimulation generator to target sites within brain 28 as well as sense brain signals within brain 28. However, IMD 16 may also use a separate set of sensing electrodes to sense the bioelectrical brain signals. In some examples, the sensing circuitry of IMD 16 may sense bioelectrical brain signals via one or more of the electrodes 24, 26 that are also used to deliver electrical stimulation to brain 28. In other examples, one or more of electrodes 24, 26 may be used to sense bioelectrical brain signals while one or more different electrodes 24, 26 may be used to deliver electrical stimulation.

Programmer 14 is an external device that is configured to wirelessly communicate with IMB 16 as needed to provide or retrieve therapy information. Programmer 14 is an external computing device that the user, e.g., the clinician and/or patient 12, may use to communicate with IMB 16. For example, programmer 14 may be a clinician programmer that the clinician uses to communicate with IMD 16 and program one or more therapy programs for IMD 16. In addition, or instead, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device, voice activation, or another input mechanism that allows the user to navigate through the user interface of programmer 14 and provide input. If programmer 14 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, programmer 14 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure medical device programmer. A wireless adapter coupled to the computing device may enable secure communication between the computing device and IMB 16.

When programmer 14 is configured for use by the clinician, programmer 14 may be used to transmit programming information to IMB 16. Programming information may include, for example, hardware information, such as the type of leads 20, the arrangement of electrodes 24, 26 on leads 20, the position of leads 20 within brain 28, one or more therapy programs defining therapy parameter values, therapeutic windows defining upper and lower amplitude limits for one or more electrodes 24, 26, and any other information that may be useful for programming into IMD 16. Programmer 14 may also be capable of completing functional tests (e.g., measuring the impedance of electrodes 24, 26 of leads 20).

The clinician may also generate and store therapy programs within IMD 16 with the aid of programmer 14. Programmer 14 may assist the clinician in the creation/identification of therapy programs by providing a system for identifying potentially beneficial therapy parameter values. For example, during a programming session, the physician may select an electrode combination for delivery of therapy to the patient. The physician may have the option to create several therapy programs. Some programs may have the same electrode combination (but different values of at least one other therapy parameter) and these therapy programs may be organized into subsets, each subset having the same electrode combination. The physician may select an efficacious therapy program for each subset based on a displayed list of sensed LFP signals from electrode combinations. The clinician may select a therapy program based on a list displayed on external programmer 14 of combinations of electrodes providing the largest LFP spectral power to provide therapy to patient 12 to address symptoms associated with the patient condition.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12.

Whether programmer 14 is configured for clinician or patient use, programmer 14 is configured to communicate with IMD 16 and, optionally, another computing device, via wireless communication. Programmer 14, for example, may communicate via wireless communication with IMD 16 using radio frequency (RF) and/or inductive telemetry techniques that may comprise techniques for proximal, mid-range, or longer-range communication. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards, or memory sticks. Further, programmer 14 may communicate with IMD 16 and another programmer via remote telemetry techniques known in the art, communicating via a personal area network (PAN), a local area network (LAN), wide area network (WAN), public switched telephone network (PSTN), or cellular telephone network, for example.

Therapy system 10 may be implemented to provide chronic stimulation therapy to patient 12 over the course of several months or years. However, therapy system 10 may also be employed on a trial basis to evaluate therapy before committing to full implantation. If implemented temporarily, some components of therapy system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates therapy system 10 provides effective treatment to patient 12, the clinician may implant a chronic stimulator within patient 12 for relatively long-term treatment. In another example, a clinician in an operating room may obtain acute recordings during lead placement and before coupling the lead with an IMD. In this example, an external device (e.g., an external electrophysiology system) may couple to the medical lead in order to obtain sensed electrical signals.

While DBS may successfully reduce symptoms of some neurological diseases, the stimulation may also cause unwanted side effects, also referred to herein as adverse effects. Side effects may include incontinence, tingling, loss of balance, paralysis, slurred speech, loss of memory, loss of inhibition, and many other neurological problems. Side effects may be mild to severe. DBS may cause one or more adverse effects by inadvertently providing electrical stimulation pulses to anatomical regions near the targeted anatomical region. These anatomical regions may be referred to as regions associated with adverse stimulation effects. For this reason, a clinician may program IMD 16 with a therapy program (or a plurality of therapy programs) that defines stimulation parameter values that balance effective therapy and minimize side effects. For example, a clinician may select an electrode(s) to deliver stimulation that did not sense the largest LFP spectral power if the electrode(s) that did sense the largest LFP spectral poser is located in a region associated with adverse stimulation effects or if the largest LFP spectral power is too high for patient comfort.

With the aid of programmer 14 or another computing device, a clinician may select values for therapy parameters for therapy system 10, including an electrode combination. By selecting particular electrodes of electrodes 24, 26 and electrode combinations for delivering electrical stimulation therapy to patient 12, a clinician may modify the electrical stimulation therapy to target one or more particular regions of tissue (e.g., specific anatomical structures) within brain 28 and avoid other regions of tissue within brain 28. In addition, by selecting values for the other stimulation parameter values that define the electrical stimulation signal, e.g., the amplitude, pulse width, and pulse rate, the clinician may generate an efficacious therapy for patient 12 that is delivered via the selected electrode subset. Due to physiological diversity, condition differences, and inaccuracies in lead placement, the parameter values may vary between patients.

During a programming session, the clinician may determine one or more therapy programs that may provide effective therapy to patient 12. Patient 12 may provide feedback to the clinician as to the efficacy of the specific program being evaluated, that may include information regarding adverse effects of delivery of therapy according to the specific program. In some examples, the patient feedback may be used to determine a clinical rating scale score. Once the clinician has identified one or more programs that may be beneficial to patient 12, patient 12 may continue the evaluation process and determine which program best alleviates the condition of patient 12 or otherwise provides efficacious therapy to patient 12. Programmer 14 may assist the clinician in the creation/identification of therapy programs by providing a methodical system of identifying potentially beneficial therapy parameters.

In another example, lead 20 may be implanted directly at the target tissue (e.g., in a region with the strongest beta oscillation or largest amplitude of a target frequency). In another example, lead 20 may be implanted based purely on anatomy alone (e.g., placed in the STN). In either of these examples, due to various uncertainties associated with the lead placement procedure, the location of the medical lead may not be the same as the region generating the maximal signal source, resulting in an offset between the target anatomy and the lead location. However, it is not necessary for lead 20 to be offset from the target anatomy as a lead placed at the target tissue that generates the strongest signal may provide effective stimulation therapy. A clinician may choose to implant lead 20 offset from target tissue or directly at or within the target tissue that generates the strongest signal.

When using medical leads with larger number of electrodes, the time necessary for a review by a clinician grows. Further, the exploration and programming time required for directional stimulation across multiple combinations of electrodes increases as well. To reduce the time required of the patient and the clinician, in some examples, a representation of signal strength sensed by multiple combinations of electrodes may be displayed to the clinician. The clinician may then select, or the system may automatically select, electrodes to provide electrical stimulation based on the sensed signals (e.g., the electrodes that sensed the greatest signal strength).

In some examples, a device (e.g., IMD 16) includes sensing circuitry configured to sense electrical signals from a first plurality of electrode combinations, each of the first plurality of electrode combinations comprising a same reference electrode of a first lead and at least one, different sense electrode of a second lead. In some examples, the device also includes processing circuitry configured to record the sensed electrical signals from the first plurality of electrode combinations, provide representations of the recorded sensed electrical signals, receive an indication, from a clinician, of two or more selected electrodes, and control delivery of electrical stimulation via the two or more selected electrodes.

These sensed electrical signals for the particular patient from combinations of electrodes 24 and/or electrodes 26 may be represented on a display or user interface (not shown in FIG. 1) at programmer 14, and/or another computing device. A clinician may select an electrode combination to provide stimulation therapy based on sensed signals from a plurality of different electrode combinations. For instance, a clinician may select an electrode combination including a combination of one or more of electrodes 24 and an electrode on IMD 16 (e.g., a case electrode or can electrode), a combination of one or more of electrodes 26 and an electrode on IMD 16, a combination of two or more of electrodes 24, a combination of two or more of electrodes 26, or a combination of one or more of electrodes 24 and one or more of electrodes 26.

IMD 16 may be configured to deliver electrical stimulation to the particular patient via the clinician selected electrode combination. As one example, where a clinician selects the electrode combination, the clinician may select the therapy to deliver electrical stimulation to the particular patient via the selected electrode combination. As yet another example, the clinician may input the selected electrode combination to programmer 14 such that programmer 14 automatically selects a therapy and configures IMD 16 to deliver electrical stimulation to the particular patient via the selected electrode combination. As yet another example, the clinician may use a computing device to select an electrode combination that may be communicated to programmer 14 that may configure IMD 16 to deliver electrical stimulation to the particular patient via the clinician-selected electrode combination.

Figure 2:
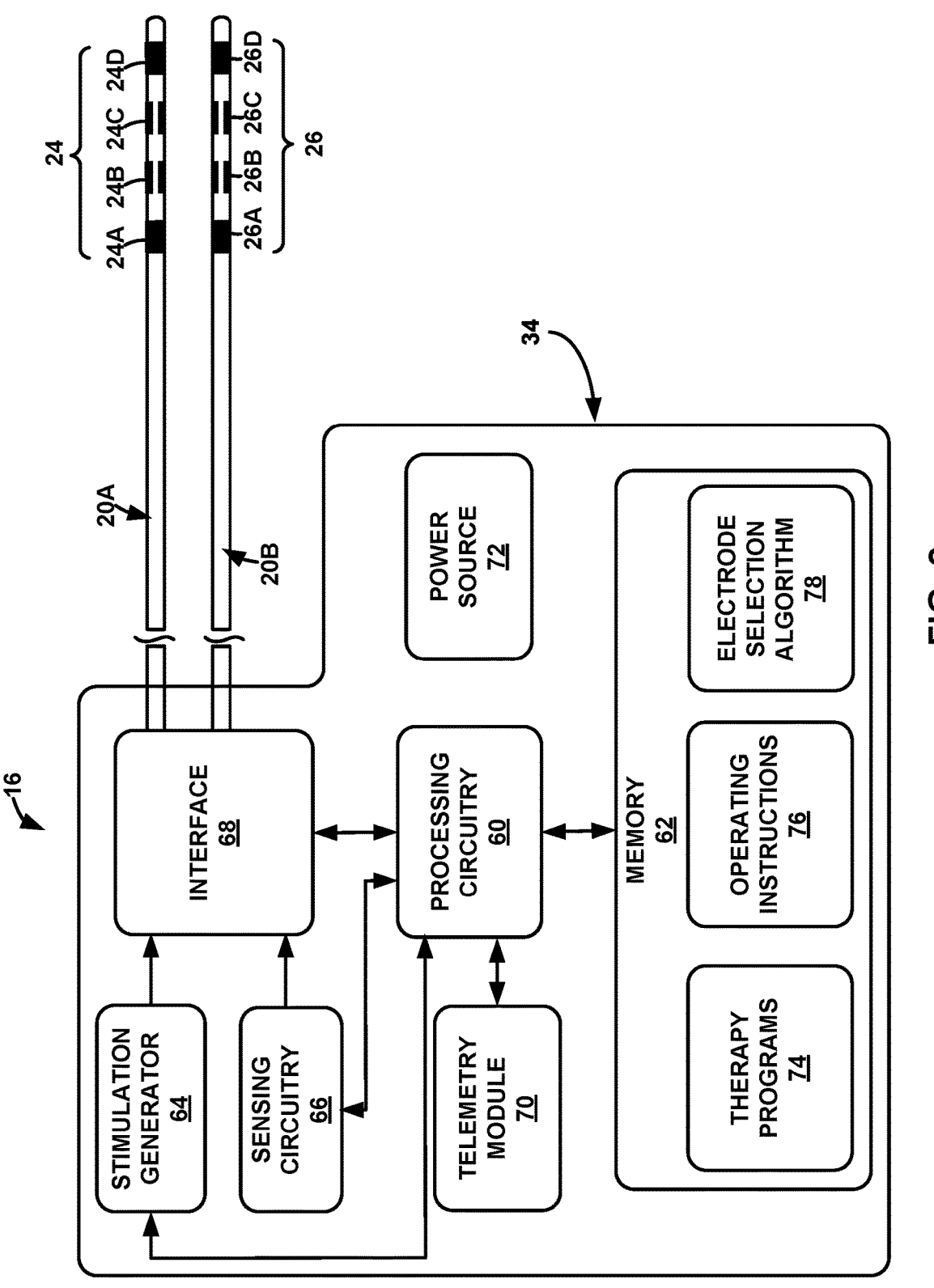
FIG. 2 is functional block diagram illustrating components of an example medical device.

FIG. 2 is functional block diagram illustrating components of an example IMD 16. In the example shown in FIG. 2, IMD 16 includes processing circuitry 60, memory 62, stimulation generator 64, sensing circuitry 66, interface 68, telemetry module 70, and power source 72. Memory 62, as well as other memories described herein, may include any volatile or non-volatile media, such as a random-access memory (RAM), read only memory (ROM), non-volatile RAM (NVRAM), electrically erasable programmable ROM (EEPROM), flash memory, and the like. Memory 62 may store computer-readable instructions that, when executed by processing circuitry 60, cause IMD 16 to perform various functions described herein.

In the example shown in FIG. 2, memory 62 may store therapy programs 74, operating instructions 76, and electrode selection algorithm 78, e.g., in separate memories within memory 62 or separate areas within memory 62. Each stored therapy program 74 defines a particular program of therapy in terms of respective values for electrical stimulation parameters, such as an electrode combination, current or voltage amplitude, and, if stimulation generator 64 generates and delivers stimulation pulses, the therapy programs may define values for a pulse width and pulse rate (i.e., frequency) of a stimulation signal. Each stored therapy program 74 may also be referred to as a set of stimulation parameter values. Operating instructions 76 guide general operation of IMD 16 under control of processing circuitry 60 and may include instructions for monitoring brain signals within one or more brain regions via electrodes 24, 26 and delivering electrical stimulation therapy to patient 12. As discussed in further detail below and in accordance with one or more techniques of this disclosure, in some examples, memory 62 may store electrode selection algorithm 78, that may include instructions that are executable by processing circuitry 60 to select two or more electrodes to sense electrical stimulation. For instance, electrode selection algorithm 78 may be executable by processing circuitry 60 to select one or more electrode combinations of electrodes 24 and/or electrodes 26 to sense physiological signals and/or deliver electrical stimulation in accordance with the techniques of FIGS. 6 and/or 7. In some examples, electrode selection algorithm 78 may be executable by processing circuitry 60 to select or suggest one or more electrode combinations of electrodes 24 and/or electrodes 26 to sense physiological signals and/or deliver electrical stimulation automatically based on the sensed electrical signals. In some examples, electrode selection algorithm 78 may be executable by processing circuitry 60 to select one or more electrode combinations of electrodes 24 and/or electrodes 26 to sense physiological signals and/or deliver electrical stimulation based on input from a user, such as a clinician.

Stimulation generator 64, under the control of processing circuitry 60, generates stimulation signals for delivery to patient 12 via selected combinations of electrodes 24, 26. In some examples, stimulation generator 64 generates and delivers stimulation signals to one or more target regions of brain 28 (FIG. 1), via a selected electrode combination from electrodes 24, 26, based on one or more stored therapy programs 74. In some examples, therapy programs 74 are chosen at programmer 14 and/or an external computer and transferred to IMD 16 and stored in memory 62. The target tissue sites within brain 28 for stimulation signals or other types of therapy and stimulation parameter values may depend on the patient condition for which therapy system 10 is implemented to manage. While stimulation pulses are described, stimulation signals may be of any form, such as continuous-time signals (e.g., sine waves) or the like.

The processors described in this disclosure, including processing circuitry 60, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processing circuitry 60 is configured to control stimulation generator 64 according to therapy programs 74 stored by memory 62 to apply particular stimulation parameter values specified by one or more programs, such as amplitude, pulse width, and pulse rate.

In the example shown in FIG. 2, the set of electrodes 24 of lead 20A includes electrodes 24A-24D, and the set of electrodes 26 of lead 20B includes electrodes 26A-26D. Processing circuitry 60 may interface 68 to apply the stimulation signals generated by stimulation generator 64 to a selected electrode combination from electrodes 24 and/or electrodes 26. In some examples, interface 68 may include individual voltage or current sources and sinks coupled to each electrode (i.e., a separate voltage and/or current source and sink for each of electrodes 24 and/or electrodes 26). In some examples, interface 68 may include a switch module that may couple stimulation signals to selected conductors within leads 20, that, in turn, deliver the stimulation signals across selected electrodes 24 and/or electrodes 26. In the example where interface 68 includes a switch module, the switch module may be a switch array, switch matrix, multiplexer, or any other type of switching module configured to selectively couple stimulation energy to selected electrodes 24 and/or electrodes 26 and to selectively sense bioelectrical brain signals with selected electrodes 24 and/or electrodes 26. In some examples, a switch module may be used to couple sensing electrodes of electrodes 24 and/or 26 to sensing circuitry 66, but not to couple stimulation electrodes of electrodes 24 and/or 26 to stimulation generator 64. Hence, stimulation generator 64 is coupled to electrodes 24 and/or electrodes 26 via interface 68 and conductors within leads 20.

As discussed above, processing circuitry 60 may control interface 68 to apply the stimulation signals generated by stimulation generator 64, or sense electrical signals by sensing circuitry 66, to a selected electrode combination of electrodes 24 and/or electrodes 26. In some examples, the selected electrode combination may be monopolar. In other words, one or more electrodes (e.g., one or more cathodes) may be located on lead 20A and the other electrode (e.g., an anode) may be located on lead 20B. In some examples, the selected electrode combination of electrodes 24 and/or electrodes 26 may be unipolar. For instance, a unipolar selected combination may include one electrode of either electrodes 24 or electrodes 26 in combination with an electrode on the housing of IMD 16 (i.e., case or can), where one is an anode and the other is a cathode. In some examples, the selected electrode combination of electrodes 24 and/or electrodes 26 may be bipolar. As one example, a bipolar selected combination may include two electrodes from electrodes 24, where one is an anode and the other is a cathode. As another example, a bipolar selected combination may include two electrodes from electrodes 26, where one is an anode and the other is a cathode. As another example, a bipolar selected combination may include an electrode from electrodes 24 and an electrode from electrodes 26, where one is an anode and the other is a cathode. In some examples, the selected electrode combination of electrodes 24 and/or electrodes 26 may be multipolar. As one example, a multipolar selected combination may include multiple anodes and/or multiple cathodes selected from electrodes 24. As another example, a multipolar selected combination may include multiple anodes and/or multiple cathodes selected from electrodes 26. As one example, a multipolar selected combination may include multiple anodes and/or multiple cathodes selected from electrodes 24 and electrodes 26.

Stimulation generator 64 may be a single channel or multi-channel stimulation generator. In particular, stimulation generator 64 may be capable of delivering a single stimulation pulse, multiple stimulation pulses or continuous signal at a given time via a single electrode combination or multiple stimulation pulses at a given time via multiple electrode combinations. In some examples, however, stimulation generator 64 and interface 68 may be configured to deliver multiple channels on a time-interleaved basis. For example, interface 68 may serve to time divide the output of stimulation generator 64 across different electrode combinations at different times to deliver multiple programs or channels of stimulation energy to patient 12.

Sensing circuitry 66, under the control of processing circuitry 60, is configured to sense bioelectrical brain signals of patient 12 via a selected subset of electrode combinations with one or more electrodes 24 and/or electrodes 26 and at least a portion of a conductive outer housing 34 of IMD 16, an electrode on an outer housing of IMD 16 or another reference. Processing circuitry 60 may control interface 68 to electrically connect sensing circuitry 66 to selected electrodes 24 and/or electrodes 26. In this way, sensing circuitry 66 may selectively sense bioelectrical brain signals with different combinations of electrodes 24 and/or electrodes 26 (and/or a reference other than an electrode of electrodes 24 and/or electrodes 26).

Although sensing circuitry 66 is incorporated into a common housing 34 with stimulation generator 64 and processing circuitry 60 in FIG. 2, in other examples, sensing circuitry 66 is in a separate outer housing from outer housing 34 of IMD 16 and communicates with processing circuitry 60 via wired or wireless communication techniques.

Telemetry module 70 is configured to support wireless communication between IMD 16 and a programmer 14 or another computing device under the control of processing circuitry 60. Processing circuitry 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62, as discussed above. Telemetry module 70 in IMD 16, as well as telemetry modules in other devices and systems described herein, such as programmer 14, may accomplish communication by RF communication techniques. In addition, telemetry module 70 may communicate with programmer 14 via proximal inductive interaction of IMD 16 with programmer 14. Accordingly, telemetry module 70 may send information to external programmer 14 on a continuous basis, at periodic intervals, or upon request from IMD 16 or programmer 14.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
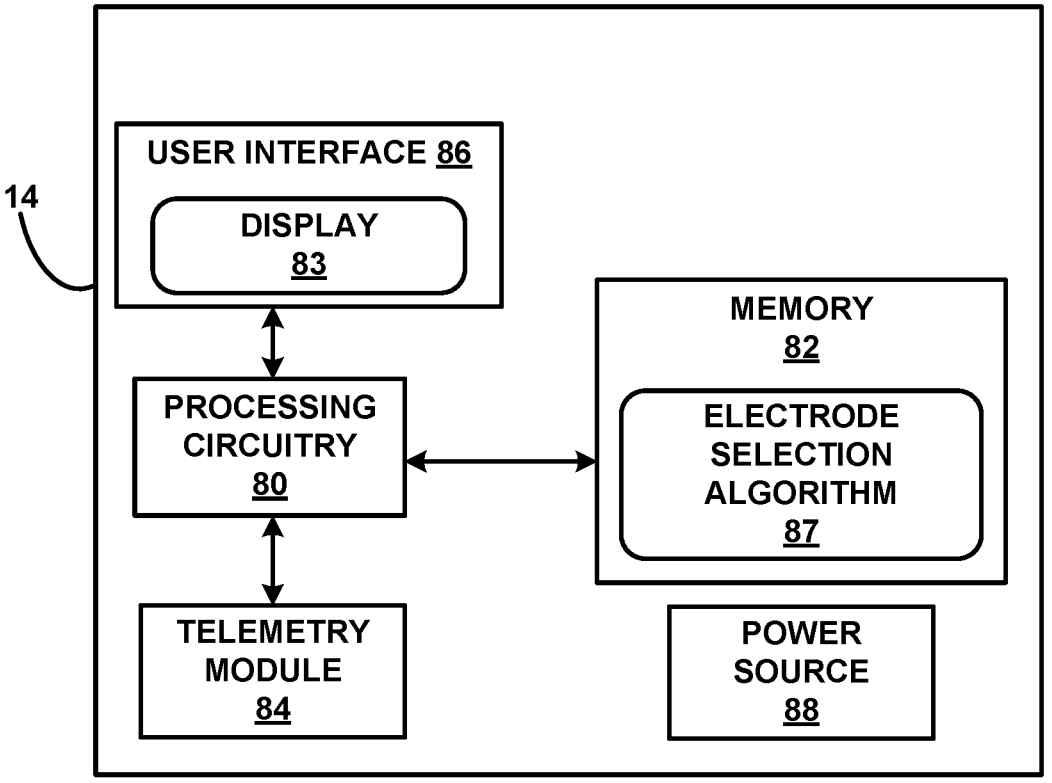
FIG. 3 is a functional block diagram illustrating components of an example medical device programmer.

FIG. 3 is a functional block diagram illustrating components of an example medical device programmer. In the example of FIG. 3, programmer 14 includes processing circuitry 80, memory 82, telemetry module 84, user interface 86 with display 83, and power source 88. Processing circuitry 80 controls user interface 86 and telemetry module 84 and stores and retrieves information and instructions to and from memory 82. Programmer 14 may be configured for use as a clinician programmer or a patient programmer. Processing circuitry 80 may comprise any combination of one or more processors including one or more microprocessors, DSPs, ASICs, FPGAs, or other equivalent integrated or discrete logic circuitry. Accordingly, processing circuitry 80 may include any suitable structure, whether in hardware, software, firmware, or any combination thereof, to perform the functions ascribed herein to processing circuitry 80.

A user, such as a clinician or patient 12, may interact with programmer 14 through user interface 86. User interface 86 includes a display 83, such as an LCD or LED display or other type of screen, with which processing circuitry 80 may present information related to the therapy (e.g., electrode combinations) and sensed electrical signals. In addition, user interface 86 may include an input mechanism to receive input from the user. The input mechanisms may include, for example, any one or more of buttons, a keypad (e.g., an alphanumeric keypad), a peripheral pointing device, a touch screen for display 83, or another input mechanism that allows the user to navigate through user interfaces presented by processing circuitry 80 of programmer 14 and provide input. In other examples, user interface 86 also includes audio circuitry for providing audible notifications, instructions or other sounds to patient 12, receiving voice commands from patient 12, or both.

Memory 82 may include instructions for operating user interface 86 and telemetry module 84, and for managing power source 88. In the example shown in FIG. 3, memory 82 also stores electrode selection algorithm 87. Electrode selection algorithm 87 may be similar to electrode selection algorithm 78 of FIG. 2. As discussed in further detail below and in accordance with one or more techniques of this disclosure, in some examples, memory 82 of programmer 14 may store electrode selection algorithm 87, that may include instructions that are executable by processing circuitry 80 to select two or more electrodes, and/or electrode combinations to sense electrical signals. For instance, electrode selection algorithm 87 may be executable by processing circuitry 80 to select two or more of electrodes and electrode combinations to sense electrical signals in accordance with the techniques described below.

In some examples, patient 12, a clinician or another user may interact with user interface 86 of programmer 14 in other ways to manually select therapy programs, or combinations of electrodes, generate new therapy programs, modify therapy programs, transmit the new programs to IMD 16, or any combination thereof.

Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of programmer 14 with IMD 16. This wireless communication is possible through the use of telemetry module 84. Accordingly, telemetry module 84 may be similar to the telemetry module contained within IMD 16. In other examples, programmer 14 may be capable of infrared communication or direct communication through a wired connection. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate.

While various information is illustrated and described as stored in memory 82 of programmer 14, it will be understood that some or all of this information may alternatively or additionally be stored within memory 62 of IMD 16. Moreover, at least some of the functionality ascribed to processing circuitry 80 of programmer 14 may instead or additionally be ascribed to processing circuitry 60 of IMD as discussed below (and vice versa).

Figures 4A, 4B:
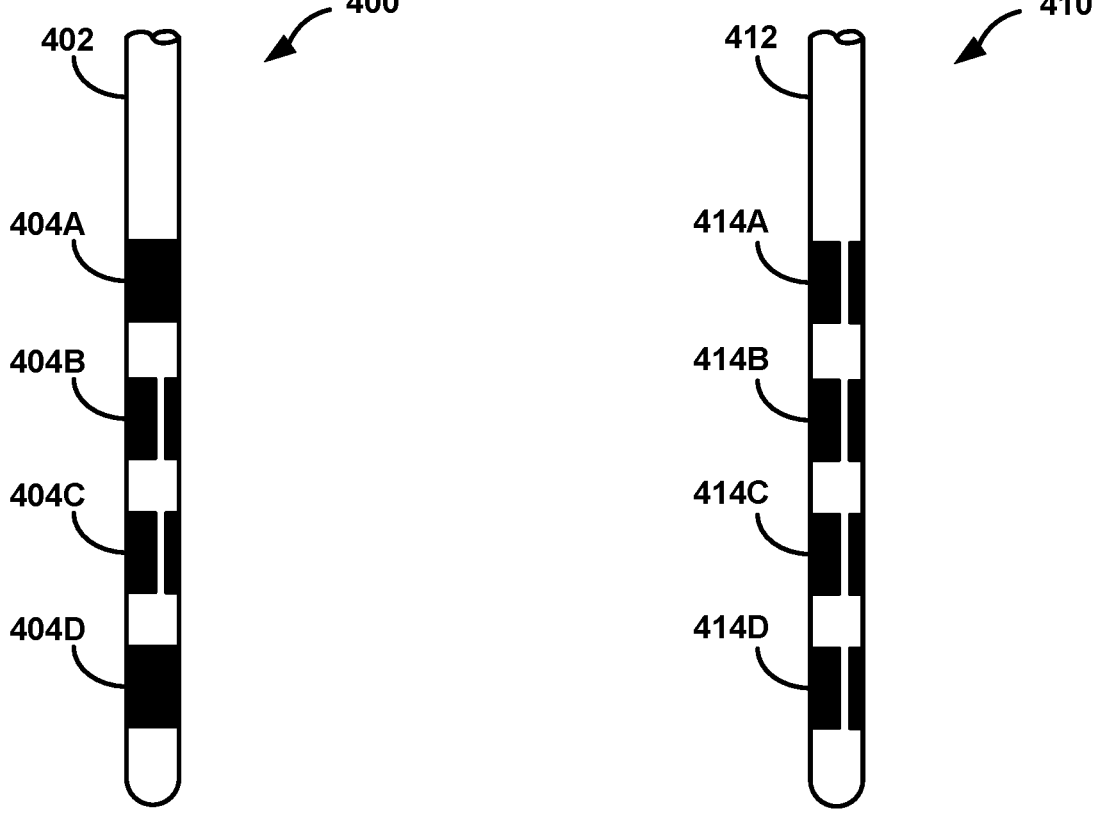
FIGS. 4A and 4B are conceptual diagrams of example leads with respective electrodes carried by the lead.

FIGS. 4A and 4B are conceptual diagrams of example leads 400 and 410, respectively, with respective electrodes carried by the lead. As shown in FIGS. 4A and 4B, leads 400 and 410 are example configurations that may be similar to leads 20 shown in FIG. 1. As shown in FIG. 4A, lead 400 includes four axial electrode levels 404 (includes electrode levels 404A-404D) positioned at various lengths along a body of lead housing 402. Lead 400 is inserted into through cranium 32 to a target position within brain 28.

Lead 400 is implanted within brain 28 at a location determined by the clinician to be near an anatomical region to be stimulated. Electrode levels 404A, 404B, 404C, and 404D may be equally spaced along the axial length of lead housing 402 at different axial positions. Each electrode level 404A-404D may have one, two, three, or more electrodes located at different angular positions around the circumference (e.g., around the perimeter) of lead housing 402. As shown in FIG. 4A, electrode level 404A and 404D include a single respective ring electrode, and electrode levels 404B and 404C each include three segmented electrodes at different circumferential positions. This electrode pattern may be referred to as a 1-3-3-1 lead in reference to the number of electrodes from the proximal end to the distal end of lead 400. Electrodes of one circumferential location may be lined up on an axis parallel to the longitudinal axis of lead 400. Alternatively, electrodes of different electrode levels may be staggered around the circumference of lead housing 402. In addition, lead 400 or 410 may include asymmetrical electrode locations around the circumference, or perimeter, of each lead or electrodes of the same level that have different sizes. These electrodes may include semi-circular electrodes that may or may not be circumferentially aligned between electrode levels.

Lead housing 402 may include one or more radiopaque stripes or other radiopaque orientation markers (not shown) along the outside of the lead housing. The radiopaque stripe corresponds to a certain circumferential location that allows lead 400 to be imaged when implanted in patient 12. Using the images of patient 12, the clinician can use the radiopaque stripe as a marker for the exact orientation of lead 400 within the brain of patient 12. Orientation of lead 400 may be needed to easily program the stimulation parameters by generating the correct electrode configuration to match the stimulation field defined by the clinician. In other examples, a marking mechanism other than a radiopaque stripe may be used to identify the orientation of lead 400. These marking mechanisms may include something similar to a tab, detent, or other structure on the outside of lead housing 402. In some examples, the clinician may note the position of markings along a lead wire during implantation to determine the orientation of lead 400 within patient 12.

FIG. 4B illustrates lead 410 that includes multiple electrodes at different respective circumferential positions at each of levels 414A-414D. Similar to lead 400, lead 410 is inserted through a burr hole in cranium 32 to a target location within brain 28. Lead 410 includes lead body 412. Four electrode levels 414 (414A-414D) are located at the distal end of lead 410. Each electrode level 414 is evenly spaced from the adjacent electrode level and includes two or more electrodes. In one example, each electrode level 414 includes three, four, or more electrodes distributed around the circumference of lead body 412. Therefore, lead 410 includes electrodes 414. Each electrode may be substantially rectangular in shape. Alternatively, the individual electrodes may have alternative shapes, e.g., circular, oval, triangular, rounded rectangles, or the like.

In alternative examples, electrode levels 404 or 414 are not evenly spaced along the longitudinal axis of the respective leads 400 and 410. For example, electrode levels 404C and 404D may be spaced approximately 3 millimeters (mm) apart while electrode levels 404A and 404B are 10 mm apart. Variable spaced electrode levels may be useful in reaching target anatomical regions deep within brain 28 while avoiding potentially undesirable anatomical regions. Further, the electrodes in adjacent levels need not be aligned in the direction as the longitudinal axis of the lead, and instead may be oriented diagonally with respect to the longitudinal axis.

Leads 400 and 410 are substantially rigid to prevent the implanted lead from varying from the expected lead shape. Leads 400 or 410 may be substantially cylindrical in shape. In other examples, leads 400 or 410 may be shaped differently than a cylinder. For example, the leads may include one or more curves to reach target anatomical regions of brain 28. In some examples, leads 400 or 410 may be similar to a flat paddle lead or a conformable lead shaped for patient 12. Also, in other examples, leads 400 and 410 may have any of a variety of different polygonal cross sections (e.g., triangle, square, rectangle, octagonal, etc.) taken transverse to the longitudinal axis of the lead.

As shown in the example of lead 400, the plurality of electrodes of lead 400 includes a first set of three electrodes disposed at different respective positions around the longitudinal axis of the lead and at a first longitudinal position along the lead (e.g., electrode level 404B), a second set of three electrodes disposed at a second longitudinal position along the lead different than the first longitudinal position (e.g., electrode level 404C), and at least one ring electrode disposed at a third longitudinal position along the lead different than the first longitudinal position and the second longitudinal position (e.g., electrode level 404A and/or electrode level 404D). In some examples, electrode level 404D may be a bullet tip or cone shaped electrode that covers the distal end of lead housing 402.

FIGS. 5A-5D are transverse cross-sections of example stimulation leads having one or more electrodes around the circumference of the lead. As shown in FIGS. 5A-5D, one electrode level, such as one of electrode levels 404 and 414 of leads 400 and 410, are illustrated to show electrode placement around the perimeter, or around the longitudinal axis, of the lead. FIG. 5A shows electrode level 500 that includes circumferential electrode 502. Circumferential electrode 502 encircles the entire circumference of electrode level 500 and may be referred to as a ring electrode in some examples. Circumferential electrode 502 may be utilized as a cathode or anode as configured by a clinician through user interface 86 (FIG. 3).

FIG. 5B shows electrode level 510 that includes two segmented electrodes 512 and 514. Each electrode 512 and 514 wraps approximately 170 degrees around the circumference of electrode level 510. Spaces of approximately 10 degrees are located between electrodes 512 and 514 to prevent inadvertent coupling of electrical current between the electrodes. Smaller or larger spaces between electrodes (e.g., between 10 degrees and 30 degrees) may be provided in other examples. Each electrode 512 and 514 may be programmed to act as an anode or cathode.

FIG. 5C shows electrode level 520 that includes three equally sized segmented electrodes 522, 524 and 526. Each electrode 522, 524 and 526 encompass approximately 110 degrees of the circumference of electrode level 520. Similar to electrode level 510, spaces of approximately 10 degrees separate electrodes 522, 524 and 526. Smaller or larger spaces between electrodes (e.g., between 10 degrees and 30 degrees) may be provided in other examples. Electrodes 522, 524 and 526 may be independently programmed as an anode or cathode for stimulation.

FIG. 5D shows electrode level 530 that includes four segmented electrodes 532, 534, 536 and 538. Each electrode 532, 534, 536 and 538 covers approximately 80 degrees of the circumference with approximately 10 degrees of insulation space between adjacent electrodes. Smaller or larger spaces between electrodes (e.g., between 10 degrees and 30 degrees) may be provided in other examples. In other examples, up to ten or more electrodes may be included within an electrode level. In alternative examples, consecutive electrode levels of lead 20 may include a variety of electrode levels 500, 510, 520, and 530. For example, lead 20 (or any other lead described herein) may include electrode levels that alternate between electrode levels 510 and 530 depicted in FIGS. 5B and 5D. In this manner, various stimulation field shapes may be produced within brain 28 of patient 112. Further the above-described sizes of electrodes within an electrode level are merely examples, and the invention is not limited to the example electrode sizes.

Also, the insulation space, or non-electrode surface area, may be of any size. Generally, the insulation space is between approximately 1 degree and approximately 20 degrees of the circumference of the lead. More specifically, the insulation space may be between approximately 5 and approximately 15 degrees. In other examples, insulation space may be between approximately 10 degrees and 30 degrees or larger. Smaller insulation spaces may allow a greater volume of tissue to be stimulated. In alternative examples, electrode size may be varied around the circumference of an electrode level. In addition, insulation spaces may vary in size as well. Such asymmetrical electrode levels may be used in leads implanted adjacent or within tissues needing certain shaped stimulation fields.

Figure 6:
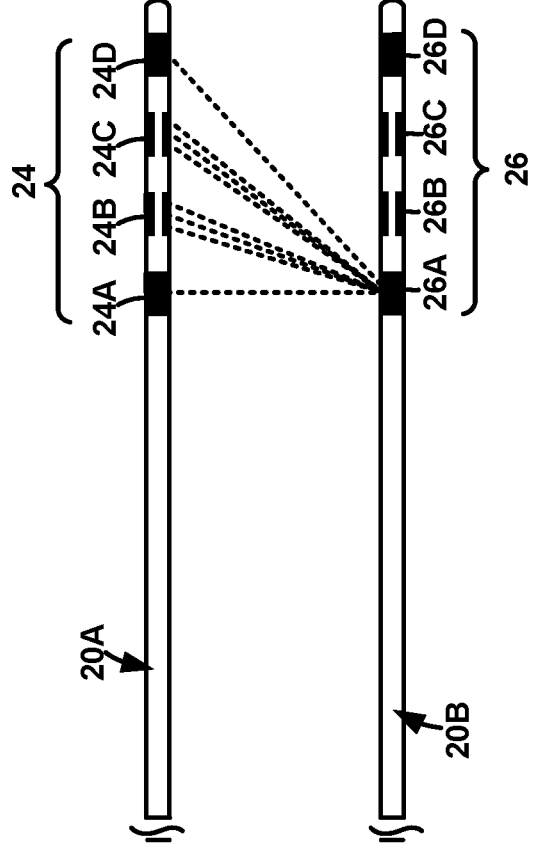
FIG. 6 is a conceptual diagram illustrating an example of monopolar sensing according to the techniques of this disclosure.

FIG. 6 is a conceptual diagram illustrating an example of monopolar sensing according to the techniques of this disclosure. Processing circuitry 60 (FIG. 2) may control electrodes 24 and 26 of leads 20 to sense electrical signals from a first plurality of electrode combinations. Each of these first plurality of electrode combinations may include a same reference electrode of a plurality of electrodes. In some examples, the reference electrode is on a first lead (e.g., lead 20B). In some examples, the first lead (e.g., the lead having the reference electrode) is a pain lead configured to treat pain in a patient. In some examples, the first lead has a relatively low impedance, such as on the order of 350 Ohms. Each of these first plurality of electrode combinations may also include a different sense electrode. In some examples, each of the different sense electrodes may be on a second lead (e.g., lead 20A). For example, electrode 26A may be configured to be the reference electrode and each of electrodes 24A, 24B, 24C, 24C may be configured to sense electrical signals referencing electrode 26A. In other examples, any electrode of lead 20B or any combination of electrodes of lead 20B may be configured to be the reference electrode. In this example, electrode 26A is a ring electrode, as are electrodes 24A and 24D. Electrodes 24B and 24C each include multiple electrodes (e.g., partial ring electrodes or segmented electrodes) located at different positions around the perimeter of the lead. While the reference electrode in the example of FIG. 6 is a ring electrode, the reference electrode may be one or more segments of a segmented electrode, such as a segmented electrode in ring mode.

In some examples, processing circuitry 60 may control electrodes 24 and 26 to sense electrical signals using the first plurality of electrode combinations in a two-step manner. For example, processing circuitry 60 may control electrodes 24 and 26 to sense electrical signals using each segment of the electrodes having multiple electrodes of lead 20A separately while referencing electrode 26A. For example, electrodes 24B and 24C may be similar to electrode level 520 of FIG. 5C and each include three electrodes. In one step, sensing circuitry 66 may sense electrical signals using the following electrode combinations: the first electrode of 24B-26A, the second electrode of 24B-26A, the third electrode of 24B-26A, the first electrode of 24C-26A, the second electrode of 24C-26A, and the third electrode of 24C-26A. In another step, processing circuitry 60 may control electrodes 24 to sense electrical signals using each electrode(s) at different axial positions along a length of lead 20A separately referencing electrode 26A. In this other step, processing circuitry 60 may sense electrical signals using the following electrode combinations: 24A-26A, 24B (in ring mode)-26A, 24C (in ring mode)-26A, and 24D-26A. In this manner, sensing circuitry 66 (FIG. 2) may be configured to sense electrical signals from each electrode with reference to the reference electrode (e.g., electrode 26A) separately in one step and sense electrical signals from all electrodes at each different axial position with reference to the reference electrode in another step. In other words, sensing circuitry 66 may be configured to sense electrical signals from each individual electrode or segment with reference to the reference electrode in one step, and sense electrical signals from every electrode at an axial position (e.g., a ring electrode or any segmented electrodes operating in ring mode) at each different axial position with reference to the reference electrode in the other step as set forth in this paragraph. These specific combinations and the two-step process are disclosed as examples. Any combinations of electrodes from lead 20A and any same electrode or same combination of electrodes on lead 20A may be used in any order and in any number of steps according to the techniques of this disclosure. By referencing a same reference electrode during sensing for each of the first plurality of electrode combinations, the sensing may be referred to as monopolar sensing, according to the techniques of this disclosure.

In some examples, there may be a single lead or more than two leads. In the case of a single lead, each electrode of the lead may be used to sense electrical signals referencing a same electrode that is on the same lead, but relatively far from the sensing electrodes, for example, referencing a more distal, distal most, more proximal, or proximal most electrode or referencing an electrode on the housing of IMD 16 (i.e., case or can). In some examples, a lead may include a lead extension. For example, if only lead 20A was present, each of electrodes 24B (in ring mode, separately, or in any combination), 24C (in ring mode, separately, or in any combination), and 24D may sense electrical signals referencing electrode 24A. In some examples, with a single lead, the axial separation between the reference electrode and any other electrode on the lead may be greater than the separation between any other electrodes on the lead. In the case of more than two leads, electrodes of each lead may be used to sense electrical signals referencing electrode 26A. Alternatively, electrodes of a given lead may be used to sense electrical signals referencing a same electrode on any other lead. For example, electrodes of a third lead may be used to sense electrical signals referencing electrode 24A, rather than 26A. By referencing a same reference electrode during sensing for each of the first plurality of electrode combinations, the sensing may be referred to as monopolar sensing, according to the techniques of this disclosure.

In some examples, after sensing circuitry 66 senses the electrical signals, processing circuitry 60 may apply noise reduction techniques to the sensed electrical signals. For example, processing circuitry 60 may be configured to reduce noise in the sensed electrical signals. In some examples, processing circuitry 60 may apply a lowest power spectral density subtraction (LPS) technique. With the LPS technique, processing circuitry 60 may determine the sensed electrical signal that has the lowest energy in the beta band and subtract that signal from each of the other sensed electrical signals. By processing circuitry 60 applying LPS, the order of highest to lowest sensed LFP may be largely the same even when using a different electrode as the reference electrode. Additionally, processing circuitry 60 may remove quiet background noise, such as a 10 Hz artifact, by applying LPS.

In some examples, processing circuitry 60 may apply the LPS technique in two steps. First, processing circuitry 60 may calculate a power spectral density plot and determine the lowest power spectral density in a given frequency band. For example, the frequency band may be a programmable band with the lower and upper limit of the band being between 1 Hz and 100 Hz inclusive. In one example, the frequency band may be 8-30 Hz. Second, processing circuitry 60 may perform a point-by-point subtraction in a time domain recording. For example, if the data is recorded at a sampling frequency of 250 Hz, then processing circuitry 60 may subtract each sampled data point for a given recorded signal from the signal determined to be the lowest power spectral density in the given frequency band. In this manner, processing circuitry 60 may, by applying LPS, retain a same order of highest to lowest sensed LFP even when using different reference electrodes.

In another example, processing circuitry 60 may apply a common average reference to the sensed electrical signals. Applying a common average reference may include determining an average of all sensed electrical signals and subtracting that average from each of the sensed electrical signals. In some instances, the order of highest to lowest amplitude of sensed LFP may change based on which electrode is selected as the reference electrode. By process circuitry 60 applying a common average reference to the sensed electrical signals, the order of highest to lowest sensed LFP may be largely the same even when using a different electrode as the reference electrode.

Figure 7:
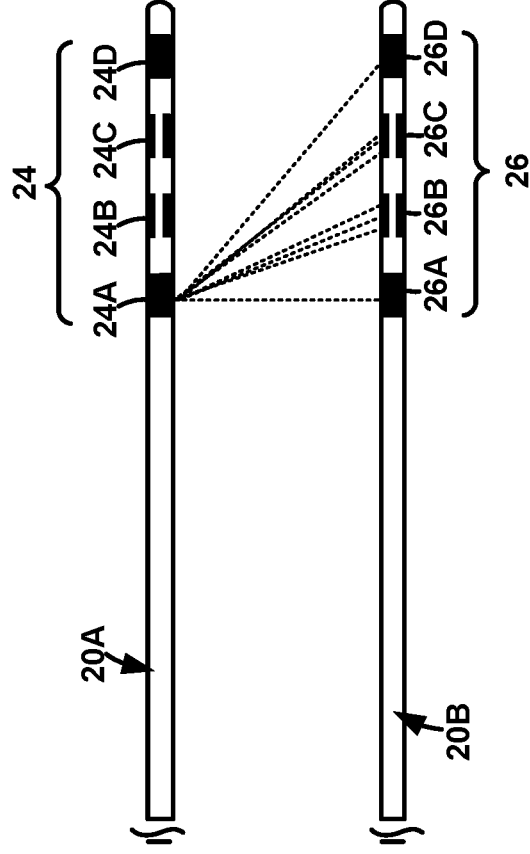
FIG. 7 is a conceptual diagram illustrating another example of monopolar sensing according to the techniques of this disclosure.

FIG. 7 is a conceptual diagram illustrating another example of monopolar sensing according to the techniques of this disclosure. The techniques of FIG. 7 may be used with the techniques of FIG. 6 or separately. Processing circuitry 60 (FIG. 2) may control electrodes 24 and 26 of leads 20 to sense electrical signals from a second plurality of electrode combinations. Each of these second plurality of electrode combinations may include a same reference electrode of the second lead (e.g., lead 20A) and a different sense electrode of the first lead (e.g., lead 20B). For example, electrode 24A may be configured to be the reference electrode and each of electrodes 26 may be configured to sense electrical signals referencing electrode 24A. In other examples, any electrode of lead 20A or any combination of electrodes of lead 20A may be configured to be the reference electrode. In this example, electrode 24A is a ring electrode, as are electrodes 26A and 26D. Electrodes 26B and 26C each include multiple electrodes (e.g., partial ring electrodes or segmented electrodes) located at different positions around the perimeter of the lead. While the reference electrode in the example of FIG. 7 is a ring electrode, the reference electrode may be one or more segments of a segmented electrode, such as a segmented electrode in ring mode.

In some examples, processing circuitry 60 may control electrodes 24 and 26 to sense electrical signals using the second plurality of electrode combinations in a two-step manner. For example, processing circuitry 60 may control electrodes 24 and 26 to sense electrical signals using each segment of the electrodes having multiple electrodes of lead 20B separately while referencing electrode 24A. For example, electrodes 24B and 24C may be similar to electrode level 520 of FIG. 5C and each may include three electrodes. In this step, sensing circuitry 66 may sense electrical signals using the following electrode combinations: the first electrode of 26B-24A, the second electrode of 26B-24A, the third electrode of 26B-24A, the first electrode of 26C-24A, the second electrode of 26C-24A, the third electrode of 26C-24A. In another step, processing circuitry 60 may control electrodes 26 to sense electrical signals using each electrode(s) at different axial positions along a length of lead 20B separately referencing electrode 24A. In this step, processing circuitry 60 may sense electrical signals using the following electrode combinations: 26A-24A, 26B (in ring mode)-24A, 26C (in ring mode)-24A, and 26D-24A. In this manner, sensing circuitry 66 (FIG. 2) may be configured to sense electrical signals from each electrode with reference to the reference electrode (e.g., electrode 24A) separately in one step and sense electrical signals from all electrodes at each different axial position with reference to the reference electrode in another step. In other words, sensing circuitry 66 may be configured to sense electrical signals from each individual electrode or segment with reference to the reference electrode in one step, and sense electrical signals from every electrode at an axial position (e.g., a ring electrode or any segmented electrodes operating in ring mode) at each different axial position with reference to the reference electrode in the other step as set forth in this paragraph.

These specific combinations and the two-step process are disclosed as examples. Any combinations of electrodes from lead 20B and any same electrode or same combination of electrodes on lead 20B may be used in any order and in any number of steps according to the techniques of this disclosure.

For example, the first lead (e.g., lead 20B) may include electrodes at different axial positions along a length of the second lead and at different circumferential positions around a perimeter of the second lead. Sensing circuitry 66 (FIG. 2) may be configured to sense electrical signals from each electrode with reference to the reference electrode (e.g., electrode 24A) separately and sense electrical signals from all electrodes at each different axial position with reference to the reference electrode. By referencing a same reference electrode during sensing for each of the first plurality of electrode combinations, the sensing may be referred to as monopolar sensing, according to the techniques of this disclosure.

In some examples, after sensing circuitry 66 senses the electrical signals, processing circuitry 60 may apply noise reduction techniques to the sensed electrical signals. For example, processing circuitry 60 may be configured to reduce noise in the sensed electrical signals. For example, processing circuitry 60 may apply a common average reference to the sensed electrical signals. In some instances, the order of highest to lowest sensed LFP may change based on which electrode is selected as the reference electrode. By applying a common average reference to the sensed electrical signals, the order of highest to lowest sensed LFP may be largely the same even when using a different electrode as the reference electrode.

In some examples, processing circuitry 60 or processing circuitry 80 may control display 83 to display the sensed electrical signals along with imaging data. In this manner, the display may facilitate visualization, by a clinician, or the LFP related to a target tissue site. For example, if the electrode sensing the highest amplitude LFP is near a region associated with adverse stimulation effects, the clinician may select a different electrode, e.g., as a cathode, for stimulation in order to reduce the chance patient 12 suffers undesirable side effects during stimulation therapy. In some examples, a clinician may use the displayed monopolar sensed, according to the techniques of FIGS. 6 and/or 7, electrical signals to verify lead placement.

In some examples, sensing circuitry 66 may sense monopolar signals of patient 12 with patient 12 in different states. For example, sensing circuitry 66 may sense monopolar signals of patient 12 in a state of rest, in a moving state, in a sleeping state, and the like. In some examples, sensing circuitry may sense monopolar signals of patient 12 in different postures, such as sitting, standing, prone, etc. These sensed monopolar electrical signals may be used by a clinician to program different therapy programs that may be used on patient 12 when patient 12 is in a given state or in a given posture. For example, sensing circuitry 66 may be configured to sense a state or posture of patient 12 (e.g., using an accelerometer or other sensor(s)) and automatically switch to a therapy program designed by the clinician for that state or posture of patient 12.

In some examples, a clinician may track the monopolar sensed electrical signals over time to determine whether a change in the disease state of patient 12 has occurred or whether patient 12 has developed a new comorbidity. In some examples, a clinician may track the monopolar sensed electrical signals over time to determine whether a lead has shifted or rotated, lead integrity has been compromised, or the like.

Figure 8:
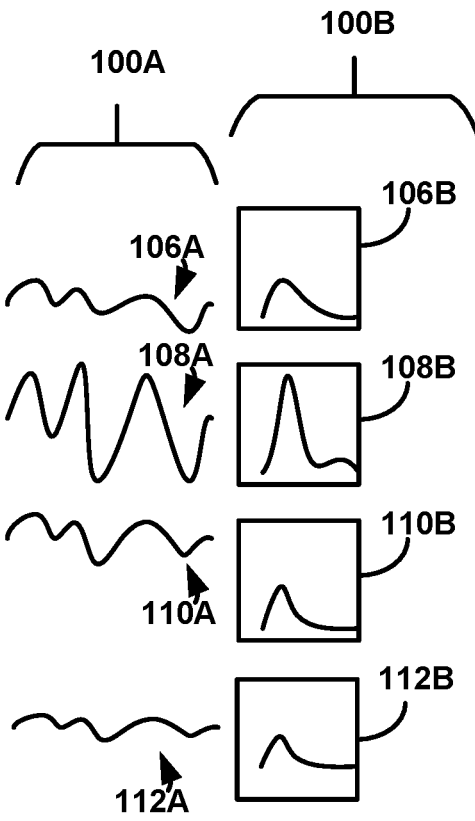
FIG. 8 is a conceptual diagram of example waveform amplitudes sensed by electrode combinations located at different axial positions along the length of a medical lead in accordance with one or more techniques of this disclosure.

FIG. 8 is a conceptual diagram of example monopolar waveform amplitudes sensed by electrode combinations between a reference electrode on a first lead and different electrodes on a second lead according to the techniques of this disclosure. As shown in the example of FIG. 8, waveform amplitudes 106A, 108A, 110A, and 112A (collectively "waveform amplitudes 100A") are examples of electrical signal information from respective electrode combinations. Spectral powers 106B, 108B, 110B, and 112B (collectively "spectral powers 100B") are additional, or alternative, examples of electrical signal information. Each of waveform amplitudes 100A and spectral powers 100B may be determined from electrical signals sensed by a respective electrode combination. Further, spectral powers 100B may be represented in a similar manner to that of FIG. 8 on display 83 (FIG. 3) to a clinician during an electrode combination selection process. That is to say, in one example, spectral powers 100B may also be represented by display 83 for a clinician to observe spectral powers 100B of waveform amplitudes 100A.

Waveform amplitude 106A may be sensed between electrode 24A and electrode 26A (FIG. 6) and spectral power 106B may be the spectral power representation of waveform amplitude 106A. Waveform amplitude 108A may be sensed between electrode 24B (in ring mode) and electrode 26A and spectral power 108B may be the spectral power representation of waveform amplitude 108A. Waveform amplitude 110A may be sensed between electrode 24C (in ring mode) and electrode 26A and spectral power 110B may be the spectral power representation of waveform amplitude 110A. Waveform amplitude 112A may be sensed between electrode 24D and electrode 26A and spectral power 112B may be the spectral power representation of waveform amplitude 112A. For example, waveform amplitudes may be sensed between any sensing electrodes (or combination thereof) on one lead and a reference electrode (or a combination of electrodes) on another lead.

In an example of the present disclosure, sensing circuitry 66 (FIG. 2) may be configured to sense electrical signals, such as waveform amplitudes 100A, from a plurality of electrode combinations. Processing circuitry 60 (FIG. 2) may be configured to identify, based on sensed electrical signals, such as waveform amplitudes 100A, an electrode combination associated with the largest amplitude or spectral power (e.g., in the Beta range).

In the example of FIG. 8, processing circuitry 60 (FIG. 2) has identified a plurality of electrode combinations that a clinician or the processing circuitry 60 may choose from. In some examples, each spectral power 100B identified by processing circuitry 60 may be displayed on display 83 (FIG. 3) and a clinician may select an electrode combination providing a spectral power 100B showing the largest detection of waveform amplitudes 100A in an axial direction. For example, in FIG. 8, spectral power 108B shows the largest magnitude of power to frequency. Spectral power 108B is a representation of waveform 108A, which is sensed between electrodes 24B (in ring mode) and electrode 26A. At display 83 (FIG. 3) a clinician may then select spectral power 108B as the strongest signal representation electrodes 24B (in ring mode) and electrode 26A as the best between all electrode combinations. This selection, by the clinician, of electrode 24B (in ring mode) and electrode 26A is the clinician's choice of electrode combination to be used for delivery of stimulation.

Figure 9:
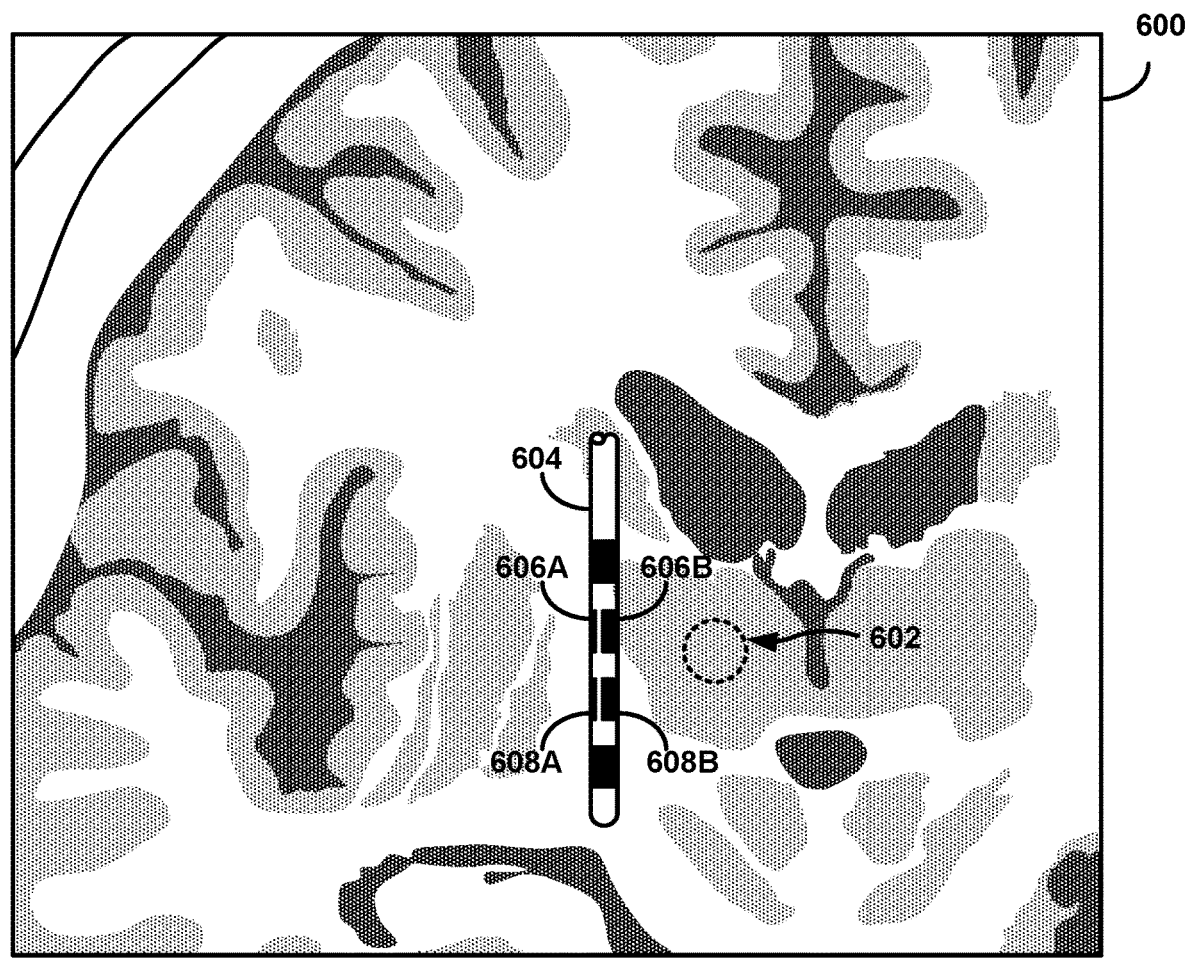
FIG. 9 is a coronal view of example tissue with a lead placed with respect to a target location within tissue.

FIG. 9 is a coronal view of example tissue with a lead 604 placed offset with respect to a target location within tissue. As shown in FIG. 9, a representation of anatomical regions of brain 28 is displayed by coronal view 600. Coronal view 600 is a front-back vertical section of brain 28. Coronal view 600 may be an actual image of brain 28 produced with magnetic resonance imaging (MRI), computed tomography (CT), or another imaging modality. Coronal view 600 may be an illustration of the location of a lead with respect to a target tissue from which electrical signals originate (e.g., LFP signals). In some examples, coronal view 600 may be presented by programmer 14, for example on display 83, or another device to indicate the relative position of lead 604 and the electrodes carried by the lead according to the sensed electrical signals. These images thus may be used to produce the anatomical regions needed to help the clinician program the stimulation parameters.

Coronal view 600 is a 2D coronal slice of brain 28. Differently shaded portions of coronal view 600 indicate varying densities of tissue within brain 28. Darker portions indicate less dense tissue. For example, the darkest portion of coronal view 600 is indicative of spaces within brain 28 that contain cerebral spinal fluid (CSF). White portions of brain 28 indicate dense tissue and more neurons. It should be noted that coronal view 600 is only an example, and actual images may include a wider range of shades and higher image resolution. Coronal view 600 provides a first perspective of the lead and the anatomical region in which the lead is implanted.

As shown in FIG. 9, lead 604 may be a lead icon that represents an actual lead implanted within patient 12. Lead 604 includes electrodes such as electrodes 606A and 606B located at the same longitudinal position and different circumferential positions around the perimeter of lead 604. Electrode 606C cannot be seen because it is located in the backside of lead 604. Similarly, lead 604 includes electrodes such as electrodes 608A and 608B located at the same longitudinal position and different circumferential positions around the perimeter of lead 604. Electrode 608C cannot be seen because it is located on the backside of lead 604. When electrical signals, such as LFP signals originate from target tissue 602, the largest amplitude and power of the signal will likely be sensed by the electrode or electrodes closest to target tissue 602. In some examples, monopolar sensing may result in electrode 606B sensing the highest amplitude of electrical signals from target tissue 602. If lead 604 moves with respect to tissue, a different electrode, such as electrode 606A (for lead rotation) or electrode 608B (for longitudinal lead movement), may not sense electrical signals with the largest amplitude.

Leads, such as lead 604, may be offset from a signal-source, such as target tissue 602. As stated above, lead 604 is offset from the signal-source so that electrodes 606A, 606B, 608A and 608B are all implanted at a distance from the signal-source. This offset may enable identification of the direction of the signal-source because different electrodes are different distances from the signal-source due to their respective locations along the lead. In examples of the present disclosure, target tissue 602 may be within the dorsal STN.

Figure 10:
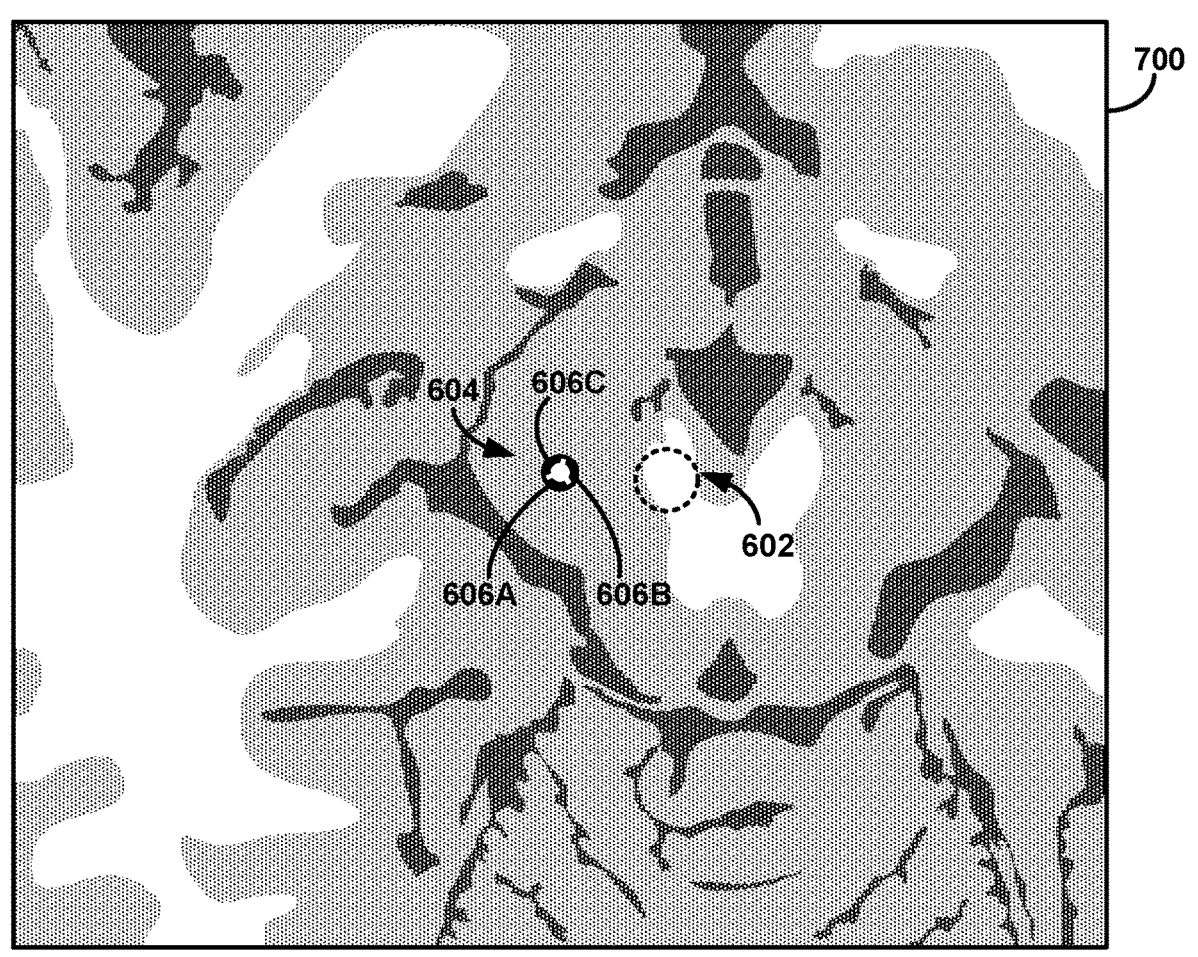
FIG. 10 is an axial view of example tissue with a lead placed with respect to a target location within tissue.

FIG. 10 is an axial view of example tissue with a lead 604 placed with respect to a target tissue 602. Axial view 700 is a different view of tissue than coronal view 600. Axial view 700 also shows the cross-sectional view of lead 604 and electrodes 606A, 606B, and 606C. As shown in axial view 700, electrode 606B is closest to target tissue 602 and may register the largest amplitude of sensed electrical signals when compared to the remaining electrodes of lead 604. If lead 604 were to rotate within tissue due to patient movement, lead pull, or some other force, a different electrode, such as electrode 606A, may be located closest to target tissue 602 and sense electrical signals with the largest amplitude when compared to other electrodes. Although the discussion of FIGS. 9 and 10 includes electrical signals that may originate in tissue, the same spatial origin may be used when sensing electrical signals evoked from delivered stimulation or sensing delivered stimulation itself for determining lead movement.

Figure 11:
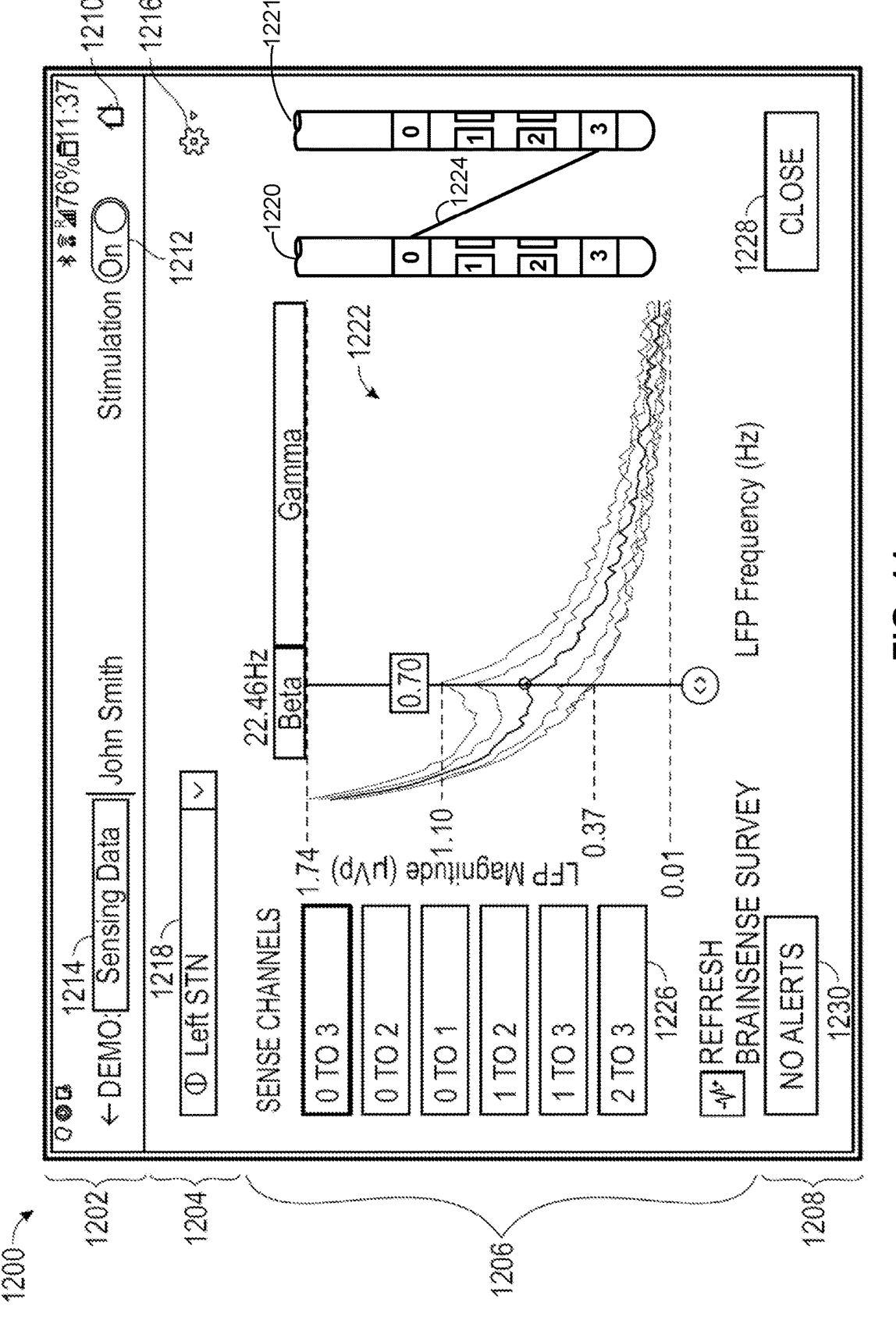
FIG. 11 illustrates an example user interface in accordance with one or more techniques of this disclosure.

FIG. 11 illustrates an example user interface display, in accordance with one or more techniques of this disclosure. User interface 1200 may be presented on display 83 of FIG. 3. User Interface 1200 may be a representation of one portion of electrode selection algorithm 87 (FIG. 3). User interface 1200 may allow a clinician to observe many aspects of a lead implantation procedure and IMD programming procedure. In some examples, user interface 1200 may also include other physical input hardware such as keyboards, mice, game pads and output hardware such as speakers, and printers. User interface 1200 may be a human-computer interface using interface layers to interact with one or more human senses, including: tactile, visual, auditory, olfactory, equilibria, and gustatory. User interface 1200 may provide a tactile and a visual user interface capable of displaying graphics.

User interface 1200 may be a standard, virtual and augmented graphical user interface. A standard display may use standard human interface devices like keyboards, mice, and computer monitors. A virtual display may block out the real world to create a virtual reality using a virtual reality interface. An augmented display may block out the real world and create an augmented reality interface.

User interface 1200 may be interactive or purely informational with a keyboard or other input device to interact with programmer 14 or other computing device, such as a mobile phone, laptop, tablet or desktop computer as discussed above. User interface 1200 may be a touch screen interactive display allowing the clinician to directly interact with programmer 14. In an example, user interface 1200 may allow clinicians to interact with programmer 14 through graphical icons and audio indicators.

The actions in user interface 1200 may be performed through direct manipulation of the graphical elements, such as by directly touching the graphical elements on a screen to perform functions. In another example, user interface 1200 may provide text-based user interfaces typed command labels or text navigation command-line interfaces where the clinician may input commands to be typed on a computer keyboard. In another example, user interface 1200 may have a combination touch screen and text-based interface.

User interface 1200 may allow a clinician to observe lead location through coronal views, such as those shown in FIGS. 9 and 10. A clinician may observe sensed LFPs. In some examples, graphical representation of leads, such as leads 20, 400, 410, and 604, and electrodes, such as electrodes 24, 26, 404, 414, 500, 510, 520, 530, 606, 608, 610 and 612 in the anatomy of the patient which may assist the physician in selecting appropriate electrodes to use for stimulation. Further, graphical representations may assist a clinician in determining an axial location of sensed LFPs as well as a direction of the sensed LFPs. By knowing an axial height and direction of the sensed LFPs, a clinician may program effective therapy for a patient in a substantially reduced period of time.

As the number of electrodes on medical leads increase, the time for monopolar review by a clinician when implanting medical leads increases. A monopolar review means the clinician is performing directional stimulation across all combinations of contacts in a monopolar fashion and then assessing the effectiveness of the stimulation. This can make the implantation and programming procedure last up to three hours or even longer. User interface 1200 may provide LFP sensed spectral power data for a clinician and allow the clinician to determine an appropriate electrode combination, thus substantially reducing the time for implantation and programming.

User interface 1200 may allow a clinician to determine, through graphical representation, relevant differences between electrode combinations by examining the spectral power between electrode combinations. User interface 1200 may assist a clinician to use LFP's spectral power to find electrode combinations closest to regions of the STN generating signals of interest, such as target tissue 602. With this information, a clinician may be better informed to program a direction of stimulation using the electrode combinations selected by the clinician based upon displayed spectral power. For example, by using a same reference electrode, the techniques of this disclosure may normalize the sensed amplitudes or powers that may be viewed by the clinician.

User interface 1200 may be comprised of a header 1202, a settings block 1204, a graphical display 1206, and a footer 1208. Header 1202 may be comprised of a home icon 1210, a stimulation status button 1212 and informational title 1214. Home icon 1210 may be a pictogram or ideogram displayed in order to help the clinician or user navigate. Home icon 1210 itself is a comprehensible symbol indicating touching home icon 1210 will take the clinician or user back to a "home", main or entry page for electrode selection algorithm 87 (FIG. 3). Home icon 120 may serve as an electronic hyperlink or file shortcut to access electrode selection algorithm 87. The clinician or user may activate home icon 1210 using mouse, pointer, finger, or voice commands.

Also, within header 1202 may be stimulation status button 1212. Stimulation status button 1212 may be both informational and functional. Stimulation status button 1212 may provide information to a clinician or user as to whether therapy system 10 is actively stimulating patient 12. Stimulation status button 1212 may brighten or even take on a bright hue, such as neon green, which may inform the clinician or user therapy system 10 is actively stimulating. The clinician may interact with user interface 1200, by pushing on status button 1212 to stop stimulation of patient 12. Status button 1212 may imitate a real button and slide to the left, where the button would cover the words "On" and expose the words "Off". Further, the bright color would disappear, and a neutral unlit color may appear. This would indicate to the clinician and user that therapy system 10 is no longer stimulating patient 12. Further, status button 1212 is functional in that it may control the administration of stimulation.

Informational title 1214 may provide information to the clinician about patient 12 including a name, such as "John Smith". The information title may also include the name of the procedure, such as "Sensing Data." Further, information title 1214 may also include information such as what type of procedure is being performed, such as a demonstration or an active brain sensing of LFPs. An arrow shown in information title 1214 may allow the clinician or user to move back a step in the procedure.

Settings block 1204 may have a setting icon 1216 and a lead selection window 1218. Settings icon 1216 may be a drop-down window that allows the clinician or user to manipulate electrode selection algorithm settings. Such settings may include selecting a background color for the display, inputting types of medical leads, inputting electrode configurations, modifying views or most any aspect to make the display of information more pleasing and useful to the clinician.

Selection window 1218 may allow the clinician or user to move between multiple implanted leads in patient 12. As shown in FIG. 11, a medical lead implanted in the left STN is being observed. The clinician may press on the down arrow in selection window 1218 to expose the other medical leads the clinician may want to observe in order to develop a stimulation therapy.

Graphical display 1206 may present graphical information to the clinician representative of an electrode combination selection. As may be shown in FIG. 11, two leads 1220 and 1221 are shown on the right side of user interface 1200. Graphical display 1206, as shown, may be in the process of selecting an electrode combination. Each of the axially located electrodes are listed at 0, 1, 2, and 3. Further, user interface 1200 may display to the clinician the electrode pair that is being displayed in spectral power display 1222. As shown a line 1224 is connecting electrode 0 of lead 1220 and electrode 3 of lead 1221 which may be a reference electrode, that may represent the sensing of LFPs between the upper most electrode of one lead and the lower most electrode on the other lead. Spectral power display 1222 shows a representation of sensed LFPs through electrodes 0 and 3 and displays a peak power at 22.46 Hz. The clinician may then cycle through the other combinations shown at electrode combination selection bar 1226. The clinician may cycle through each electrode combination using selection bar 1226 and pressing on the electrode combination they would like to examine. Selection bar 1226 may include all possible electrode combinations (not shown in FIG. 11). The clinician may be looking for the electrode combination providing the largest peak power on spectral power display 1222. Once the clinician has determined an electrode pair showing the greatest spectral power, the clinician may write down the electrode pair for later programming. In other examples, the clinician may press and hold on the electrode pair that is desired so as to have the electrode pair recorded in memory 82 (FIG. 3) for later use as the selected axial electrode pair for delivery of stimulation. The clinician may shift to perform the same procedure on the other lead(s) through selection window 1218 where other leads may be chosen. For example, the clinician may shift from sensing using electrodes of lead 1220 to sensing using electrodes of lead 1221 and using an electrode of lead 1220 as a reference electrode. The clinician may also press on the arrow in informational title 1214 to move to a procedure for identifying a circumferential electrode pair with a spectral power showing the best results for sensed LFPs.

Footer 1208 may have a way to exit electrode selection algorithm 78 through graphical button 1228. Button 1228 may allow a clinician to end electrode selection algorithm 78. Button 1228 may close the axial electrode selection portion of electrode selection algorithm 78. Alert window 1230 may alert the clinician or user of any therapy system alerts, patient alerts or electrode selection algorithm alerts. As shown in FIG. 11, there are no current alerts; however, should any alerts occur they may be displayed to the clinician in window 1230. Further, the alerts may be accompanied by varying types of colors depending on the urgency of the alert, such as green for a lower tier alert, yellow for a relatively important alert and red for a very important alert. Additionally, in some examples, an audible alarm may be present to gain the attention of the clinician. In another example, processing circuitry 80 or another device may generate an alert in response to determining that a significant change in level or directionality of spectral powers occurs since the last clinician visit. Such a change in the spectral powers from one or more electrode combinations may indicate potential lead damage, degradation of tissue, shift of the lead, and/or rotation of the lead. In another example, a significant change in the spectral power of electrode combinations, such as in the strength or variation across electrodes over time (e.g., from the last clinic visit), may result from neural degeneration, inflammation, or other clinically relevant physiological changes in the patient. Therefore, processing circuitry 80, another device, or the clinician, may identify changes in the patient due to changes in the level or directionality of determined spectral powers associated with one or more electrode combinations.

Figure 12A:
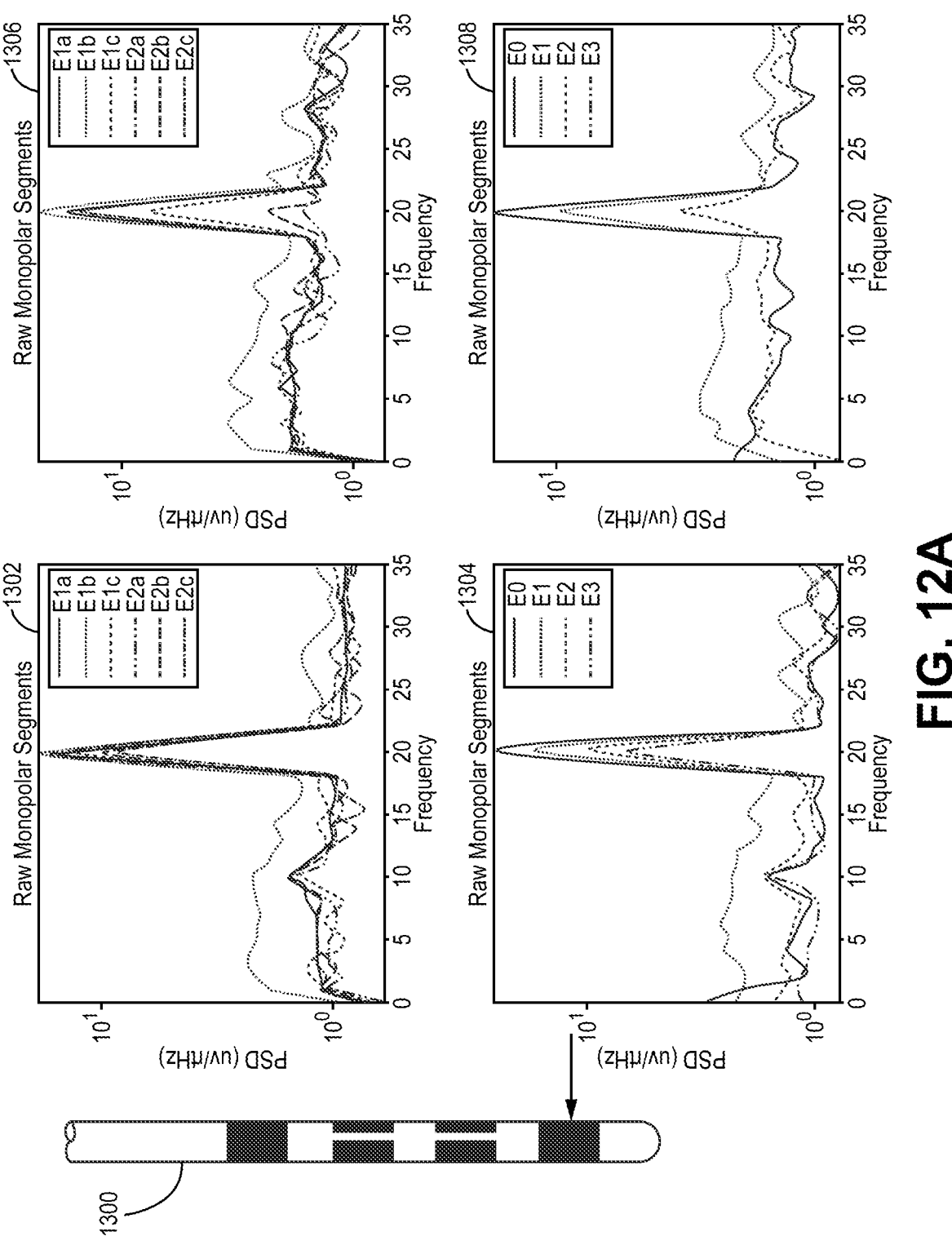
FIGS. 12A-12D illustrate example user interfaces displaying leads and power spectral densities in accordance with one or more techniques of this disclosure.

FIGS. 12A-12D illustrate example user interfaces displaying leads and power spectral densities in accordance with one or more techniques of this disclosure. In FIG. 12A, a representation of a lead is displayed in box 1300 with the bottom electrode of the lead acting as a reference electrode. Graph 1302 displays the raw power spectral density of sensed electrical signals using monopolar sensing on a segment-by-segment basis. Graph 1304 displays the raw power spectral density of the sensed electrical signals by the ring electrodes and any segmented electrodes in ring mode using monopolar sensing. Graph 1306 displays noise reduced power spectral density of the sensed electrical signals using monopolar sensing on a segment-by-segment basis. Graph 1308 displays noise reduced power spectral density of the sensed electrical signals by the ring electrodes and any segmented electrodes in ring mode using monopolar sensing.

Figure 12B:
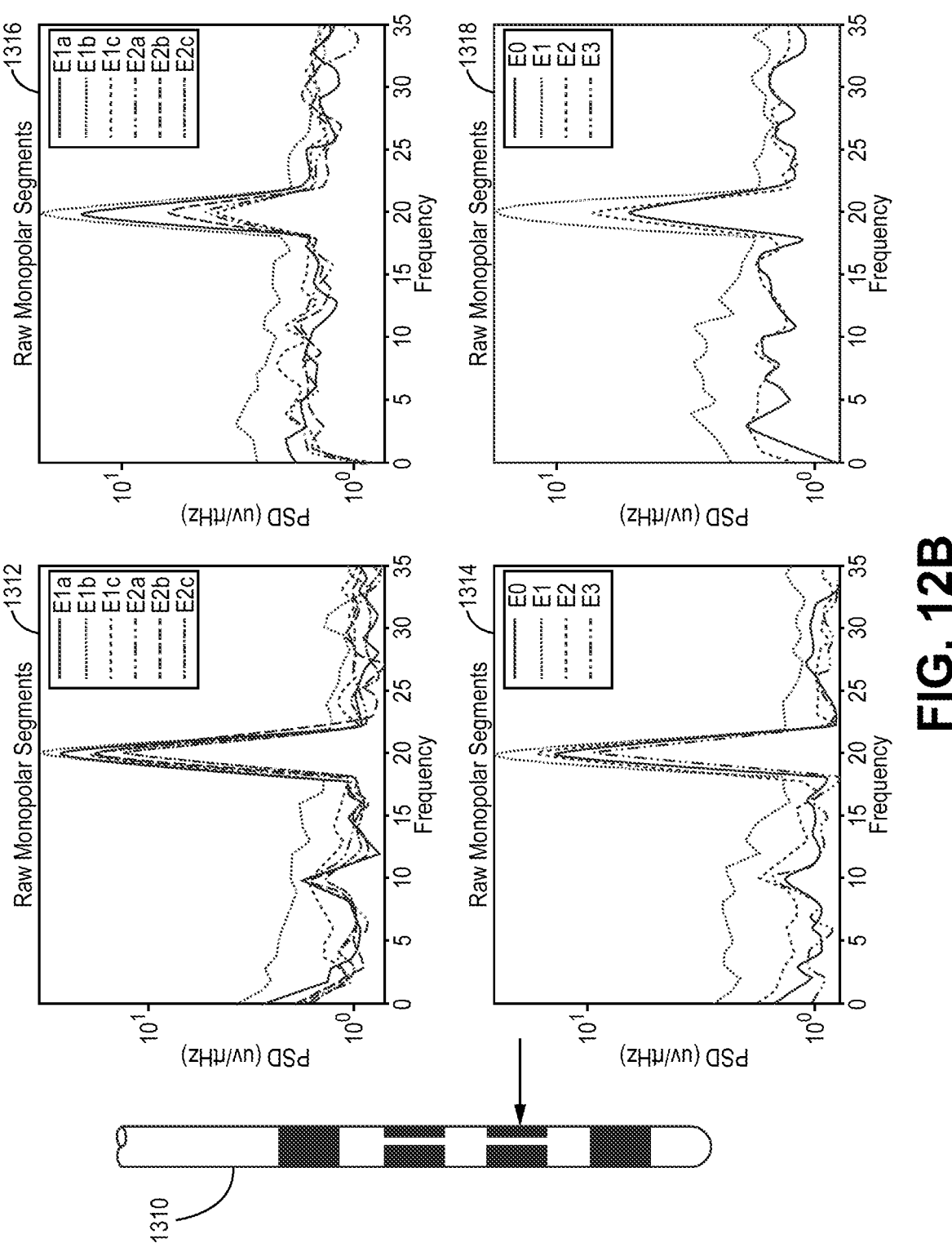

In FIG. 12B, a representation of a lead is displayed in box 1310 with the next to the bottom electrode of the lead acting as a reference electrode. Graph 1312 displays the raw power spectral density of sensed electrical signals using monopolar sensing on a segment-by-segment basis. Graph 1314 displays the raw power spectral density of the sensed electrical signals by the ring electrodes and any segmented electrodes in ring mode using monopolar sensing. Graph 1316 displays noise reduced power spectral density of the sensed electrical signals using monopolar sensing on a segment-by-segment basis. Graph 1318 displays noise reduced power spectral density of the sensed electrical signals by the ring electrodes and any segmented electrodes in ring mode using monopolar sensing.

Figure 12C:
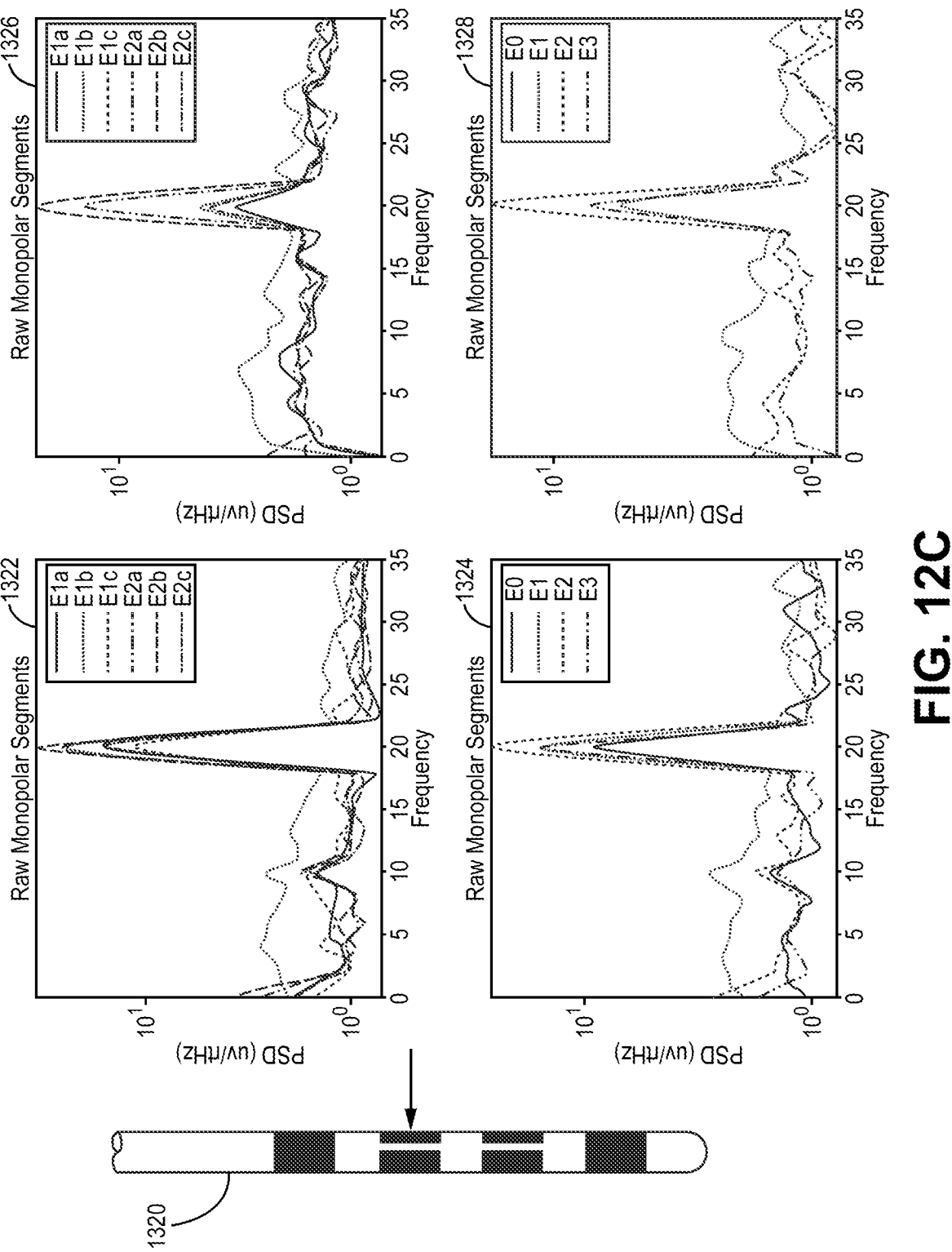

In FIG. 12C, a representation of a lead is displayed in box 1320 with the next to the top electrode of the lead acting as a reference electrode. Graph 1322 displays the raw power spectral density of sensed electrical signals using monopolar sensing on a segment-by-segment basis. Graph 1324 displays the raw power spectral density of the sensed electrical signals by the ring electrodes and any segmented electrodes in ring mode using monopolar sensing. Graph 1326 displays noise reduced power spectral density of the sensed electrical signals using monopolar sensing on a segment-by-segment basis. Graph 1328 displays noise reduced power spectral density of the sensed electrical signals by the ring electrodes and any segmented electrodes in ring mode using monopolar sensing.

Figure 12D:
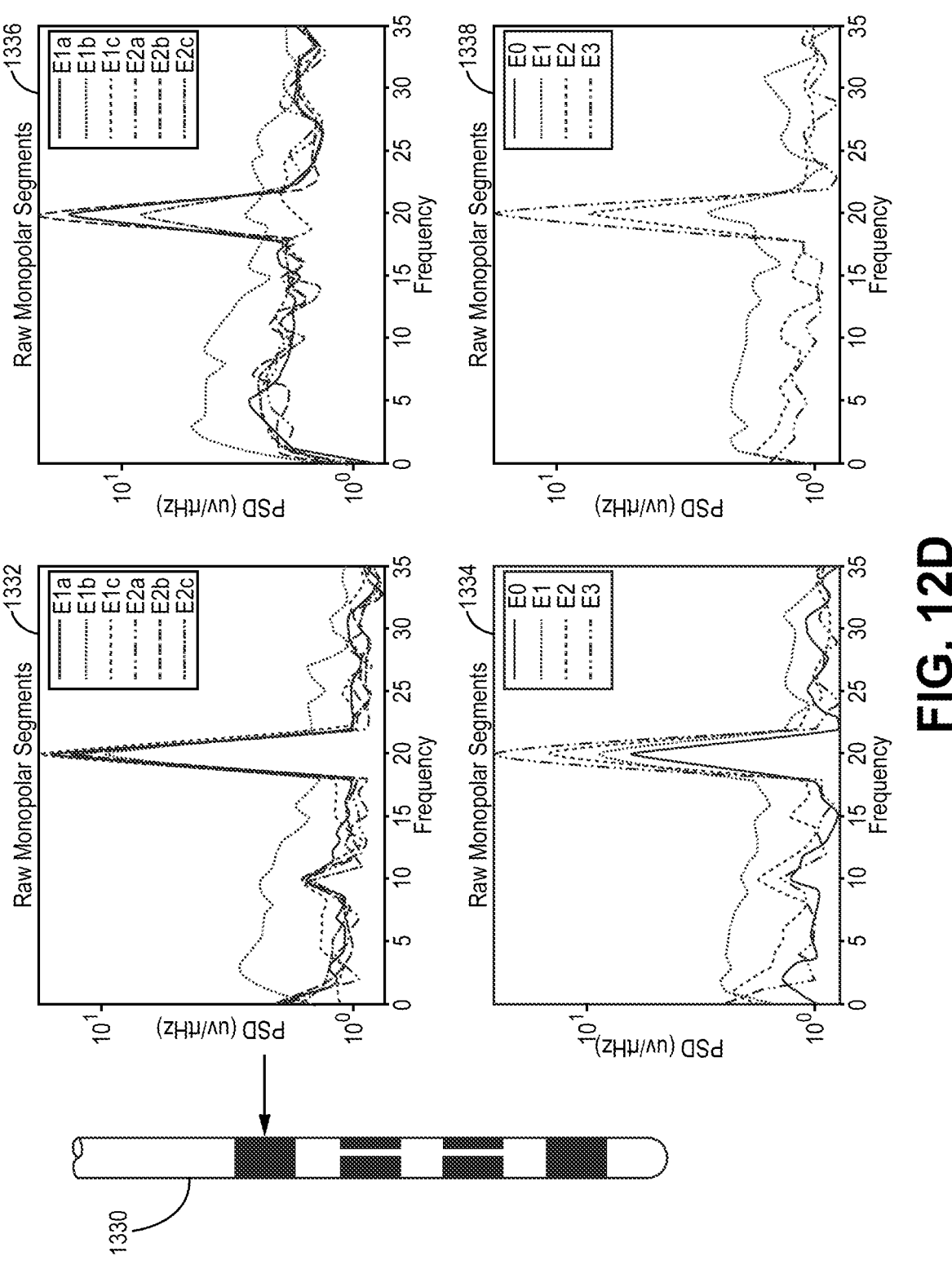

In FIG. 12D, a representation of a lead is displayed in box 1330 with the bottom electrode of the lead acting as a reference electrode. Graph 1332 displays the raw power spectral density of sensed electrical signals using monopolar sensing on a segment-by-segment basis. Graph 1334 displays the raw power spectral density of the sensed electrical signals by the ring electrodes and any segmented electrodes in ring mode using monopolar sensing. Graph 1336 displays noise reduced power spectral density of the sensed electrical signals using monopolar sensing on a segment-by-segment basis. Graph 1338 displays noise reduced power spectral density of the sensed electrical signals by the ring electrodes and any segmented electrodes in ring mode using monopolar sensing.

FIG. 13 is a flow diagram of an example technique for selecting an electrode combination to deliver electrical stimulation, in accordance with one or more techniques of this disclosure. For example, processing circuitry 80 of programmer 14, processing circuitry 60, or a processor of another computing device alone, or in combination with processing circuitry 60, may perform any part of the techniques of FIG. 13.

Processing circuitry 60 may receive electrical signals from a first plurality of electrode combinations, each of the first plurality of electrode combinations comprising a same reference electrode of a plurality of electrodes and at least one different sense electrode of the plurality of electrodes, the plurality of electrodes being associated with one or more leads (300). For examples, processing circuitry 60 may control sensing circuitry 66 and/or interface 68 to sense electrical signals through the first plurality of electrode combinations and receive from sensing circuitry 66 and/or interface 68 the sensed electrical signals.

Processing circuitry 60 may record the sensed electrical signals from the first plurality of electrode combinations (302). For example, processing circuitry 60 may store the sensed electrical signals in electrode selection algorithm 78. Processing circuitry 60 may provide representations of the recorded sensed electrical signals (304). For example, processing circuitry 60 may transmit representations of the recorded sensed electrical signals, via telemetry module 70, to programmer 14. Programmer 14 may display the representations of the recorded sensed electrical signals via display 83 for a clinician to view.

In some examples, processing circuitry 60 may receive an indication of two or more selected electrodes. For example, a clinician may provide user input selecting two or more electrodes to form an electrode combination to deliver stimulation in user interface 86 of programmer 14. For example, a clinician may select an electrode combination that may yield the highest amplitude or power. Programmer 14 may transmit the indication of two or more selected electrodes to IMD 16 via telemetry module 84. Processing circuitry 60 may receive the transmitted indication via telemetry module 70.

In some examples, processing circuitry 60 may control delivery of electrical stimulation via the two or more selected electrodes. For example, processing circuitry 60 may store the two or more selected electrodes in therapy programs 74 and may control IMD 16 to deliver electrical stimulation using a therapy program having the two or more selected electrodes from therapy programs 74.

In some examples, the sensed electrical signals comprise LFPs. In some examples, processing circuitry 60 may identify two or more suggested electrodes based on a signal strength of sensed LFPs, such as an amplitude or power of the LFPs. For example, processing circuitry may identify an electrode combination having a highest spectral power and provide an indication of the two or more suggested electrodes which may be displayed on display 83 of programmer 14. In this manner, processing circuitry 60 may make a suggestion to the clinician of two or more electrodes to be used for stimulation.

In some examples, the reference electrode is on a first lead (e.g., lead 20B) and each other electrode of the first plurality of electrode combinations is on a second lead (e.g., 20A), and wherein each electrode on the second lead (e.g., electrodes 24A-24D) is part of a respective one of the first plurality of electrode combinations.

In some examples, processing circuitry 60 may receive electrical signals from a second plurality of electrode combinations, each of the second plurality of electrode combinations comprising a same reference electrode (e.g., electrode 24A) of the second lead (e.g., lead 20A) and a different sense electrode of the first lead (e.g., lead 20B). In some examples, processing circuitry 60 may record the sensed electrical signals from the second plurality of electrode combinations.

In some examples, the second lead comprises electrodes at different axial positions along a length of the second lead (e.g., lead 20A) and at different circumferential positions around a perimeter of the second lead and wherein sensing circuitry 66 is configured to: sense electrical signals from each electrode with reference to the reference electrode (e.g., electrode 26A) separately; and sense electrical signals from all electrodes at each different axial position with reference to the same reference electrode.

In some examples, the reference electrode is a ring electrode. In some examples, the reference electrode includes one or more segments of a segmented electrode. In some examples, processing circuitry 60 is further configured to reduce noise in the sensed electrical signals and the representations of the sensed electrical signals comprise noise reduced sensed electrical signals. In some examples, processing circuitry 60 is configured to reduce noise in the sensed electrical signals by applying a common average reference to the sensed electrical signals.

In some examples, as part of providing representations of the recorded sensed electrical signals, processing circuitry 60 via processing circuitry 80 (or processing circuitry 80) is configured to control display 83 to display the representations of the recorded sensed electrical signals. In some examples, processing circuitry 60 via processing circuitry 80 (or processing circuitry 80) is further configured to control the display to display a representation of a location of the one or more leads (e.g., lead 20A and/or lead 20B). For example, display 83 may display representations of the recorded sensed electrical signals with a representation of the respective electrode as shown in FIGS. 11 and/or 12A-12D or in some other manner. For example, display 83 may display the representations of the recorded sensed electrical signals as dots, bars, or line(s) indicative of signal strength. Alternatively, or additionally, display 83 may display the representation of the recorded sensed electrical signals in a manner typically used to display wireless network signal strength, as a numerical representation of the signal strength, or the like. In some examples, processing circuitry 60 is further configured to record the sensed electrical signals periodically over time. In some examples, processing circuitry 60 is further configured to: determine a change in the sensed electrical signals over time; and based on determining the change in the sensed electrical signals, provide a notification indicative of the change in the sensed electrical signals.

Figure 14:
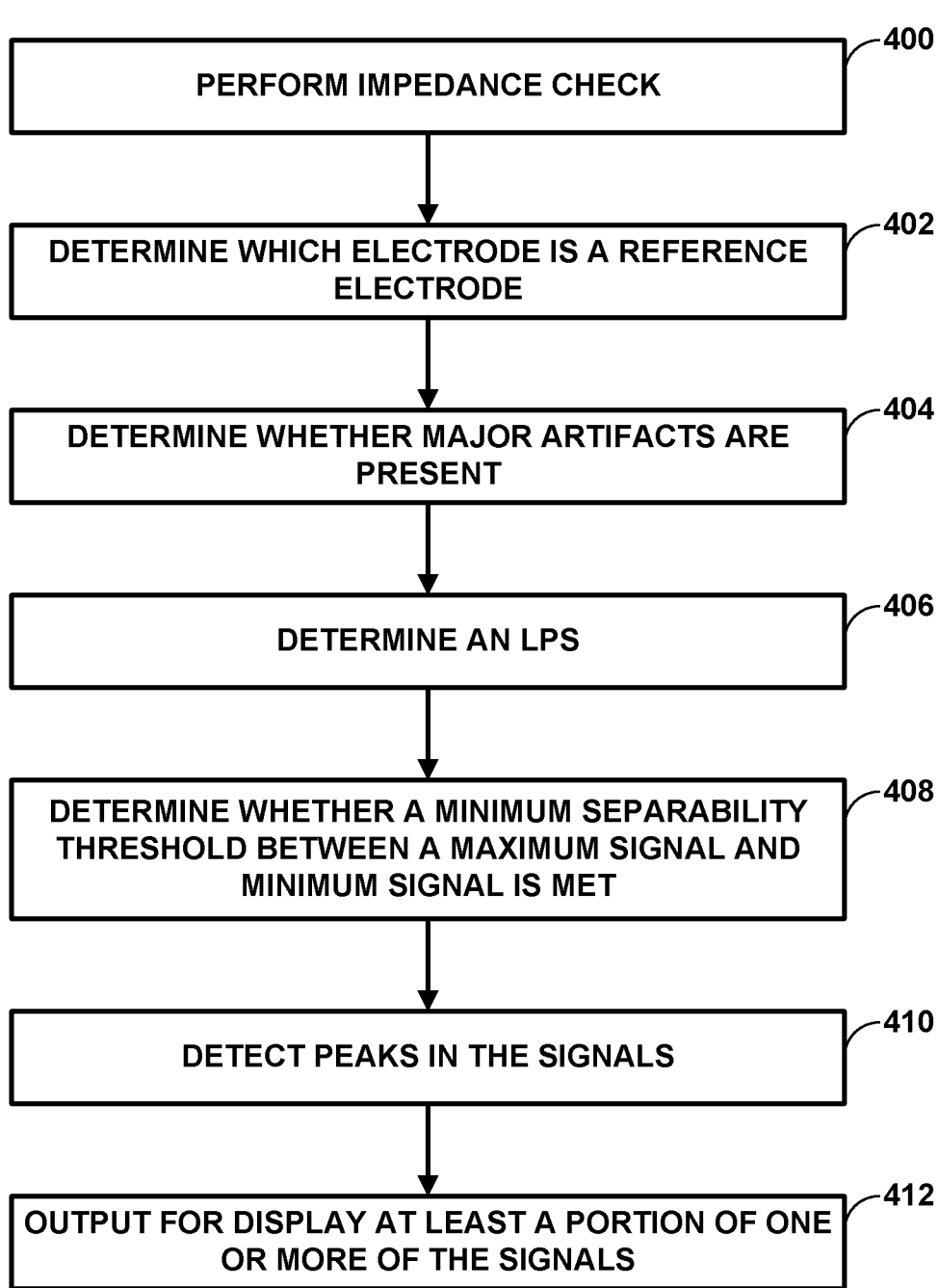
FIG. 14 is a flow diagram of an example technique for determining data to display relating to sensed signals, in accordance with one or more techniques of this disclosure.

FIG. 14 is a flow diagram of an example technique for determining data to display relating to sensed signals, in accordance with one or more techniques of this disclosure. For example, processing circuitry 80 of programmer 14, processing circuitry 60, or a processor of another computing device alone, or in combination with processing circuitry 60, may perform any part of the techniques of FIG. 14.

In the example of FIG. 14, processing circuitry 60 may perform an impedance check (400). For example, processing circuitry 60 may determine whether an impedance of each sensing electrode and the reference electrode are within a predetermined range (e.g., an acceptable operating range). This impedance check process, or a separate lead insertion detection process, may determine that each lead is inserted into IMD 16 correctly or is not inserted correctly. In some examples, if any of the impedance of the sensing electrodes or the reference electrode are not within an acceptable operating range (e.g., such as if a conductor is fractured or if each lead is not inserted into IMD 16), processing circuitry 60 may abort the monopolar techniques of this disclosure. In some examples, processing circuitry 60 may output an indication as to why the monopolar techniques are being aborted for display to a clinician, for example, via display 83 (FIG. 3) (e.g., indicating which lead and/or electrode was associated with an out of range impedance).

Processing circuitry 60 may determine which electrode is a reference electrode (402). For example, processing circuitry 60 may receive an instruction as to which electrode is the reference electrode or may read which electrode is the reference electrode from memory. In some examples, the first reference electrode may be a proximal ring electrode of the second lead (e.g., electrode 26A of lead 20B of FIG. 6).

In some examples, the reference electrode may operate in ring mode or in a directional mode.

Processing circuitry 60 may determine whether major artifacts are present in any sensed signals (404), such as artifacts caused by movement or electrical signals from the heart (e.g., signals that may be presented in an electrocardiogram), which may cause less accurate results in the sensing of signals from the brain or other target tissues. If there are major artifacts (e.g., artifacts exceeding respective thresholds), processing circuitry 60 may abort the monopolar techniques. In some examples, a clinician may override the aborting of the monopolar techniques and use such techniques even when there may be major artifacts.

Processing circuitry 60 may then determine an LPS (406). For example, processing circuitry 60 may record monopolar LFPs for a plurality of channels (e.g., 6 channels) using the reference electrode. Processing circuitry 60 may calculate a power spectral density (PSD) for each channel. Processing circuitry 60 may identify the channel with the lowest PSD power within a predefined LPS window. Processing circuitry 60 may perform point by point subtraction of the LPS channel having the lowest PSD in a time domain from all other sensed signals so as to remove a common signal originating from the reference electrode. In some examples, a resolution of 1 Hz may be used.

Processing circuitry 60 may determine whether a minimum separability threshold between a maximum signal and a minimum signal is met (408). If the minimum separability threshold is not met, the results may not be viewed as viable. In which case, processing circuitry 60 may generate an indication for output, for example, via display 83 which may be indicative of the results not being viable. In some examples, processing circuitry 60 may determine the minimum separability threshold. For example, processing circuitry 60 may determine PSD scores as 1) PSD scores=[mean($ch_1[f_1:f_2]$), mean($ch_2[f_1:f_2]$), . . . mean($ch_n[f_1:f_2]$)], determine the minimum separability threshold (MST) as 2) MST=0.25*max(PSD scores), determine the maximum difference as 3) Max Difference=max(PSD scores)−min(PSD scores), and determine that the minimum separability threshold is met when Max Difference>MST, where $ch_x$ denotes a channel, $f_1$ denotes the low frequency value of the window of interest, $f_2$ denotes the high frequency value of the window of interest, mean denotes the mean or average value for an array, max denotes the maximum value of the array, min denotes the minimum value of the array. In some examples, if the minimum separation threshold is not met, processing circuitry 60 may store and/or flag the frequency window being used.

Processing circuitry 60 may then detect one or more peaks in the signals (410). For example, processing circuitry 60 may detect peaks from LPS results sampled at 1 Hz (the 1 Hz LPS results). In some examples, processing circuitry 60 may interpolate the 1 Hz LPS results to provide continuous traces for use with a peak detection algorithm. In some examples, processing circuitry 60 may select one or more peaks having the highest magnitude for display.

Processing circuitry 60 may output for display at least a portion of one or more of the signals and/or representation of the signals sensed from one or more channels (412). For example, processing circuitry 60 may output to display 83 a portion of one or more of the re-referenced signals (e.g., the channels after the subtraction of the LPS channel having the lowest PSD) having the highest magnitude, using a certain value window (e.g., 5 Hz), centered around the one or more selected peaks. It should be noted that processing circuitry 60 may not display the channel having the lowest power PSD of the re-refenced signals because the channel having the lowest power may have been subtracted from each of the channels and such a re-referenced channel would be a straight line at zero power. In some examples, processing circuitry 60 may use an average of 1 Hz results, rather than re-performing LPS.

As described herein, a system that employs directional brain sensing may reduce the time required to identify electrode combinations for sensing desired signals and/or delivering electrical stimulation therapy. In this manner, the systems described herein may improve clinician efficiency and treatment efficacy. This process is indeed advantageous considering the use of increasing numbers of electrodes on implantable leads (e.g., leads with electrodes disposed at different positions around the perimeter of the lead and at different positions along the length of the lead). Therefore, the techniques and systems described herein may enable the use of more electrodes that may improve targeting of desired tissue (e.g., specific regions of the brain associated with a disease, symptoms, or therapy) while reducing the time necessary for programming by the clinician.

The techniques described in this disclosure, including those attributed to IMD 16, programmer 14, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored, as one or more instructions or code, on a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structures or any other structure suitable for implementation of the techniques described herein.

In addition, in some respects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques may be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

This disclosure includes the following non-limiting examples.

Example 1. An implantable medical device comprising: sensing circuitry configured to sense electrical signals from a first plurality of electrode combinations, each of the first plurality of electrode combinations comprising a same reference electrode of a plurality of electrodes and at least one different sense electrode of the plurality of electrodes, the plurality of electrodes being associated with one or more leads; and processing circuitry configured to: record the sensed electrical signals from the first plurality of electrode combinations; and provide representations of the recorded sensed electrical signals.

Example 2. The implantable medical device of example 1, wherein the processing circuitry is further configured to receive an indication of two or more selected electrodes of the plurality of electrodes.

Example 3. The implantable medical device of example 2, wherein the processing circuitry is further configured to control delivery of electrical stimulation via the two or more selected electrodes.

Example 4. The implantable medical device of any of examples 1-3, wherein the sensed electrical signals comprise sensed local field potentials (LFPs).

Example 5. The implantable medical device of example 4, wherein the processing circuitry is further configured to identify, based on signal strengths of the sensed LFPs, two or more suggested electrodes to form the two or more selected electrodes.

Example 6. The implantable medical device of any of examples 1-5, wherein the reference electrode comprises a ring electrode.

Example 7. The implantable medical device of any of examples 1-5, wherein the reference electrode comprises one or more segments of a segmented electrode.

Example 8. The implantable medical device of any of examples 1-7, wherein the reference electrode is on a first lead and each other electrode of the first plurality of electrode combinations is on a second lead, and wherein each electrode on the second lead is part of a respective one of the first plurality of electrode combinations.

Example 9. The implantable medical device of example 8, wherein the sensing circuitry is further configured to sense electrical signals from a second plurality of electrode combinations, each of the second plurality of electrode combinations comprising a same reference electrode on the second lead and at least one different sense electrode on the first lead and wherein the processing circuitry is further configured to record the sensed electrical signals from the second plurality of electrode combinations.

Example 10. The implantable medical device of example 8, wherein the second lead comprises electrodes at different axial positions along a length of the second lead and at different circumferential positions around a perimeter of the second lead and wherein the sensing circuitry is configured to: sense electrical signals from each electrode with reference to the reference electrode separately; and sense electrical signals from all electrodes at each different axial position with reference to the reference electrode.

Example 11. The implantable medical device of any of examples 1-10, wherein the processing circuitry is further configured to reduce noise in the sensed electrical signals and wherein the representations of the sensed electrical signals comprise noise reduced sensed electrical signals.

Example 12. The implantable medical device of example 11, wherein the processing circuitry is configured to reduce noise in the sensed electrical signals by applying a lowest power spectral density subtraction or a common average reference to the sensed electrical signals.

Example 13. The implantable medical device of any of examples 1-12, wherein as part of providing representations of the recorded sensed electrical signals, the processing circuitry is configured to control a display to display the representations of the recorded sensed electrical signals.

Example 14. The implantable medical device of example 13, wherein the processing circuitry is further configured to control the display to display a representation of the one or more leads.

Example 15. The implantable medical device of any of examples 1-14, wherein the processing circuitry is further configured to record the sensed electrical signals periodically over time.

Example 16. The implantable medical device of example 15, wherein the processing circuitry is further configured to: determine a change in the sensed electrical signals over time; and based on determining the change in the sensed electrical signals, provide a notification indicative of the change in the sensed electrical signals.

Example 17. The implantable medical device of any of examples 1-16, further comprising: the one or more leads; and a stimulation generator coupled to the one or more leads, wherein the stimulation generator is configured to generate electrical stimulation via the two or more selected electrodes.

Example 18. A method comprising: receiving, by processing circuitry, electrical signals from a first plurality of electrode combinations, each of the first plurality of electrode combinations comprising a same reference electrode of a plurality of electrodes and at least one different sense electrode of the plurality of electrodes, the plurality of electrodes being associated with one or more leads; recording, by the processing circuitry, the sensed electrical signals from the first plurality of electrode combinations; and providing, by the processing circuitry, representations of the recorded sensed electrical signals.

Example 19. The method of example 18, further comprising: receiving, by the processing circuitry, an indication of two or more selected electrodes of the plurality of electrodes; and controlling, by the processing circuitry, delivery of electrical stimulation via the two or more selected electrodes.

Example 20. A non-transitory computer-readable storage medium storing instructions that, when executed, cause processing circuitry to: receive electrical signals from a first plurality of electrode combinations, each of the first plurality of electrode combinations comprising a same reference electrode of a first plurality of electrodes of a first lead and at least one different sense electrode of a second plurality of electrodes of a second lead; record the sensed electrical signals from the first plurality of electrode combinations; and provide representations of the recorded sensed electrical signals.

Example 21. The implantable medical device of any of examples 1-17, wherein the processing circuitry is further configured to determine, prior to recording the sensed electrical signals from the first plurality of electrode combinations, whether an impedance of each electrode of the first plurality of electrode combinations is within a predetermined range.

Example 22. The implantable medical device of any of examples 1-17 or 21, wherein the processing circuitry is further configured to determine, prior to recording the sensed electrical signals from the first plurality of electrode combinations, whether each of the one or more leads is inserted into an INS.

Example 23. The implantable medical device of any of examples 1-17 or 21-22, wherein the processing circuitry is further configured to determine whether there are artifacts in the sensed electrical signals from the first plurality of electrode combinations.

Example 24. The implantable medical device of any of examples 1-17 or 21-23, wherein the processing circuitry is further configured to determine whether a minimum separation threshold between a maximum and minimum signal of the sensed electrical signals is met.

Example 25. The implantable medical device of example 24, wherein the processing circuitry is further configured to determine the minimum separability threshold.

Example 26. The implantable medical device of example 25, wherein as part of determining the minimum separability threshold, the processing circuitry is configured to: determine PSD scores=[mean($ch_1[f_1{:}f_2]$), mean($ch_2[f_1{:}f_2]$), mean($ch_n[f_1{:}f_2]$)]; and determine the minimum separability threshold=0.25*max(PSD scores), where $ch_x$ denotes a channel, $f_1$ denotes a low frequency value of a window of interest, $f_2$ denotes a high frequency value of the window of interest, mean denotes the mean or average value for an array, and max denotes the maximum value of the array.

Various examples of the disclosure have been described. These and other examples are within the scope of the following claims.

What is claimed is:

1. An implantable medical device comprising:
sensing circuitry configured to sense electrical signals from a first plurality of electrode combinations, each of the first plurality of electrode combinations comprising a same reference electrode of a plurality of electrodes on one or more leads and at least one different sense electrode of the plurality of electrodes, wherein a same reference electrode is on a first lead of the one or more leads and each other electrode of the first plurality of electrode combinations is on a second lead of the one or more leads, and wherein each electrode on the second lead is part of a respective one of the first plurality of electrode combinations; and
processing circuitry configured to:
record the sensed electrical signals from the first plurality of electrode combinations; and
provide representations of the recorded sensed electrical signals.

2. The implantable medical device of claim 1, wherein the processing circuitry is further configured to receive, from a user, an indication of two or more selected electrodes of the plurality of electrodes.

3. The implantable medical device of claim 2, wherein the processing circuitry is further configured to control delivery of electrical stimulation via the two or more selected electrodes.

4. The implantable medical device of claim 1, wherein the sensed electrical signals comprise sensed local field potentials (LFPs).

5. The implantable medical device of claim 4, wherein the processing circuitry is further configured to identify, based on signal strengths of the sensed LFPs, two or more suggested electrodes to form the two or more selected electrodes.

6. The implantable medical device of claim 1, wherein the same reference electrode comprises a ring electrode.

7. The implantable medical device of claim 1, wherein the same reference electrode comprises one or more segments of a segmented electrode.

8. The implantable medical device of claim 1, wherein the same reference electrode comprises a first same reference electrode, and wherein the sensing circuitry is further configured to sense electrical signals from a second plurality of electrode combinations, each of the second plurality of electrode combinations comprising a second same reference electrode on the second lead and at least one different sense electrode on the first lead and wherein the processing circuitry is further configured to record the sensed electrical signals from the second plurality of electrode combinations.

9. The implantable medical device of claim 1, wherein the second lead comprises electrodes at different axial positions along a length of the second lead and at different circumferential positions around a perimeter of the second lead and wherein the sensing circuitry is configured to:

sense electrical signals from each electrode with reference to the same reference electrode separately; and sense electrical signals from all electrodes at each different axial position with reference to the same reference electrode.

10. The implantable medical device of claim 1, wherein the processing circuitry is further configured to reduce noise in the sensed electrical signals and wherein the representations of the sensed electrical signals comprise noise reduced sensed electrical signals.

11. The implantable medical device of claim 10, wherein the processing circuitry is configured to reduce noise in the sensed electrical signals by applying a lowest power spectral density subtraction or a common average reference to the sensed electrical signals.

12. The implantable medical device of claim 1, wherein as part of providing representations of the recorded sensed electrical signals, the processing circuitry is configured to control a display to display the representations of the recorded sensed electrical signals.

13. The implantable medical device of claim 12, wherein the processing circuitry is further configured to control the display to display a representation of the one or more leads.

14. The implantable medical device of claim 1, wherein the processing circuitry is further configured to record the sensed electrical signals periodically over time.

15. The implantable medical device of claim 14, wherein the processing circuitry is further configured to:

determine a change in the sensed electrical signals over time; and based on determining the change in the sensed electrical signals, provide a notification indicative of the change in the sensed electrical signals.

16. The implantable medical device of claim 1, further comprising:

the one or more leads; and a stimulation generator coupled to the one or more leads, wherein the stimulation generator is configured to generate electrical stimulation via the two or more selected electrodes.

17. A method comprising:

receiving, by processing circuitry, electrical signals from a first plurality of electrode combinations, each of the first plurality of electrode combinations comprising a same reference electrode of a plurality of electrodes on one or more leads and at least one different sense electrode of the plurality of electrodes, wherein a same reference electrode is on a first lead of the one or more leads and each other electrode of the first plurality of electrode combinations is on a second lead of the one or more leads, and wherein each electrode on the second lead is part of a respective one of the first plurality of electrode combinations;

recording, by the processing circuitry, the sensed electrical signals from the first plurality of electrode combinations; and providing, by the processing circuitry, representations of the recorded sensed electrical signals.

18. The method of claim 17, further comprising:

receiving, from a user and by the processing circuitry, an indication of two or more selected electrodes of the plurality of electrodes; and controlling, by the processing circuitry, delivery of electrical stimulation via the two or more selected electrodes.

19. Non-transitory computer-readable storage media storing instructions that, when executed, cause processing circuitry to:

receive electrical signals from a first plurality of electrode combinations, each of the first plurality of electrode combinations comprising a same reference electrode of a plurality of electrodes on one or more leads and at least one different sense electrode of the plurality of electrodes, wherein a same reference electrode is on a first lead of the one or more leads and each other electrode of the first plurality of electrode combinations is on a second lead of the one or more leads, and wherein each electrode on the second lead is part of a respective one of the first plurality of electrode combinations;

record the sensed electrical signals from the first plurality of electrode combinations; and provide representations of the recorded sensed electrical signals.

\* \* \* \* \*